US010829558B2

(12) United States Patent
Gehlsen et al.

(10) Patent No.: US 10,829,558 B2
(45) Date of Patent: Nov. 10, 2020

(54) SMALL ANTIBODY-LIKE POLYPEPTIDES THAT BIND TO EPHA2 RECEPTOR

(71) Applicant: Research Corporation Technologies, Inc., Tucson, AZ (US)

(72) Inventors: Kurt R. Gehlsen, Tucson, AZ (US); Licia Tomei, Rome (IT); Anna Demartis, Rome (IT)

(73) Assignee: RESEARCH CORPORATION TECHNOLOGIES, INC., Tucson, AZ (US)

( * ) Notice: Subject to any disclaimer, the term of this patent is extended or adjusted under 35 U.S.C. 154(b) by 508 days.

(21) Appl. No.: 15/520,573

(22) PCT Filed: Oct. 23, 2015

(86) PCT No.: PCT/US2015/057111
§ 371 (c)(1),
(2) Date: Apr. 20, 2017

(87) PCT Pub. No.: WO2016/065258
PCT Pub. Date: Apr. 28, 2016

(65) Prior Publication Data
US 2017/0306032 A1   Oct. 26, 2017

Related U.S. Application Data

(60) Provisional application No. 62/068,471, filed on Oct. 24, 2014, provisional application No. 62/069,781, filed on Oct. 28, 2014.

(51) Int. Cl.
| | | |
|---|---|---|
| C07K 16/00 | (2006.01) | |
| C07K 16/28 | (2006.01) | |
| A61K 39/395 | (2006.01) | |
| C40B 40/10 | (2006.01) | |
| A61K 39/00 | (2006.01) | |

(52) U.S. Cl.
CPC ........ *C07K 16/2866* (2013.01); *A61K 39/395* (2013.01); *C40B 40/10* (2013.01); *A61K 2039/505* (2013.01); *C07K 16/28* (2013.01); *C07K 2317/524* (2013.01); *C07K 2318/00* (2013.01)

(58) Field of Classification Search
None
See application file for complete search history.

(56) References Cited

U.S. PATENT DOCUMENTS

| | | | |
|---|---|---|---|
| 2010/0143345 A1* | 6/2010 | Kinch | C07K 16/24 424/133.1 |
| 2012/0230981 A1* | 9/2012 | Bramhill | C07K 16/005 424/133.1 |

FOREIGN PATENT DOCUMENTS

| | | |
|---|---|---|
| WO | 2009/099961 A2 | 8/2009 |
| WO | 2011/039724 A1 | 4/2011 |
| WO | 2013/119903 A1 | 8/2013 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
International Search Report and Written Opinion dated Feb. 5, 2016 from International Application No. PCT/US2015/057111, 11 Pages.
UniProtKB/TrEMBL Accession No. F7F0D6, May 29, 2013 (online).
Extended European Search Report dated Feb. 27, 2018 for European Patent Application No. 15852472.8, 12 pages.
Chen et al., "Discovery of Novel Candidate Therapeutics and Diagnostics Based on Engineered Human Antibody Domains", Current Drug Discovery Technologies, vol. 11, No. 1, Jan. 31, 2014, pp. 28-40.
Xiao et al., "A large library based on a novel (CH2) scaffold: Identification of HIV-1 inhibitors", Biochemical and Biophysical Research Communications, vol. 387, No. 2, Sep. 18, 2009, pp. 387-392.
Ying et al., "Engineered Fc based antibody domains and fragments as novel scaffolds", Biochimica et Biophysica Acta, vol. 1844, No. 11, May 2, 2014, pp. 1977-1982.
Gehlsen et al., "Pharmacokinetics of engineered human monomeric and dimeric CH2 domains", mAbs, vol. 4, No. 4, Jul. 1, 2012, pp. 466-474.
Ullman et al., "High Affinity Binders to EphA2 Isolated from Abdurin Scaffold Libraries; Characterization, Binding and Tumor Targeting", PLOS One, vol. 10, No. 8, Aug. 27, 2015, 25 pages.

(Continued)

*Primary Examiner* — Meera Natarajan
(74) *Attorney, Agent, or Firm* — MH2 Technology Law Group, LLP

(57) ABSTRACT

The present disclosure is directed to a modified isolated immunoglobulin CH2 domain that specifically binds to an extracellular region of an EphA2 receptor, wherein the amino acid sequence of the modified immunoglobulin CH2 domain includes at least one amino acid substitution, addition or deletion in comparison to a wild type immunoglobulin CH2 domain amino acid sequence, wherein the wild type immunoglobulin CH2 domain amino acid sequence includes SEQ ID NO:1 or SEQ ID NO:2. Heterologous immunoconjugates including fusion proteins and pharmaceutical compositions including the modified isolated immunoglobulin CH2 domain are also disclosed. In addition, methods of treating a disease associated with EphA2 overexpression and methods for killing a target cell expressing EphA2 receptors using the modified isolated immunoglobulin CH2 domain are provided.

27 Claims, 20 Drawing Sheets
Specification includes a Sequence Listing.

(56) References Cited

OTHER PUBLICATIONS

Gehlsen et al., "The next generation of targeted toxins: A novel deimmunized sarcin ribotoxin fused with an EphA2 Abdurin binder", Abstract 655 from AACR 106th Annual Meeting 2015 on Apr. 18-22, 2015 in Philadelphia, PA, Cancer Research, vol. 75, No. Suppl. 15, Aug. 1, 2015, p. 655.

* cited by examiner

SMALL ANTIBODY-LIKE POLYPEPTIDES THAT BIND TO EPHA2 RECEPTOR

CROSS REFERENCE TO RELATED APPLICATIONS

This application is a U.S. National Stage application of PCT/US2015/057111 filed 23 Oct. 2015, which claims the benefit of, and relies on the filing date of, U.S. provisional patent application number 62/068,471, filed 24 Oct. 2014, and U.S. provisional patent application No. 62/069,781, filed 28 Oct. 2014, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Oct. 23, 2015, is named 0185.0002-PCT_SL.txt and is 67,920 bytes in size.

BACKGROUND

Cancer is one disease characterized by the uncontrolled proliferation of cells. While there are a number of causes for such uncontrolled proliferation, one of those causes is aberrant signaling among the cells in a tissue. These aberrant signals, often arising from altered genes or gene products, but also due to viral infection or random mutation, either stimulate or remove inhibitions on the growth of the cell and its neighbors causing rapid and uncontrolled cell division. Other signaling defects may remove usual controls on cell behavior allowing metastasis to develop, spreading the cancer to distant tissues.

Eph receptors are a family of transmembrane proteins involved in cell to cell communication. Each Eph receptor has among other components an intracellular domain with tyrosine kinase activity and an extracellular binding domain. In humans, there are 14 types of Eph receptors classified into the Eph A and Eph B families that normally interact with 8 ephrin receptor ligands found on cell surfaces. Binding of an ephrin ligand to the extracellular binding domain of an Eph receptor causes other Eph receptor molecules to cluster with that receptor molecule, activates its intracellular tyrosine kinase activity to phosphorylate certain tyrosine residues in the receptor molecule which creates binding sites for other intracellular signaling proteins. Phosphorylation also causes internalization of the receptor molecule and marks it for degradation.

The EphA2 receptor is an Eph receptor that is commonly overexpressed (or found in overabundance) on cancer cells. Ovarian, breast, prostate, lung, colon, esophageal, renal, cervical cancers and melanoma have been reported to have a much greater abundance of the receptor than non-cancerous cells in those tissues. Induced expression of the EphA2 receptor in transformed cells converts those cells to a malignant phenotype, enhances experimental metastasis of tumors derived from such cells and increases angiogenesis in those tumors.

Antibodies to the EphA2 receptor are well known. Upon binding to the extracellular binding domain of the EphA2 receptor, some act therapeutically to increase tyrosine phosphorylation and turnover of receptor and reduce tumor growth. Others have no effect on tyrosine phosphorylation (that is they do not affect ephrin A2 binding, but still are able to negatively affect tumor growth. Conjugates of these antibodies that deliver cytotoxic moieties to the cells bearing EphA2 receptors have also been described. Once delivered the cytotoxic moieties are released from the antibody to exert their toxic activity.

However, the size of antibodies and their conjugates remains a problem for delivering a sufficient amount of antibody and/or toxin to the cancer cells to effectively shrink or eliminate the tumor. Further, large size can affect the ability of the antibody to bind certain epitopes. Additionally, small antibody-like molecules, such as scFVs, while able to bind their targets, have a very short half-life. Thus, there remains a need for improved EphA2 receptor binding molecules that can affect the activity of the receptor and/or deliver toxic moieties to the cancer cell by targeting the EphA2 receptor.

BRIEF SUMMARY

The present disclosure is directed to a modified isolated immunoglobulin CH2 domain that specifically binds to an extracellular region of an EphA2 receptor, wherein the amino acid sequence of the modified immunoglobulin CH2 domain includes at least one amino acid substitution, addition or deletion in comparison to a wild type immunoglobulin CH2 domain amino acid sequence.

The present disclosure also provides a method of treating a disease associated with EphA2 overexpression, such as cancer, the method comprising: administering to a subject in need thereof a therapeutically effective dose of a modified isolated immunoglobulin CH2 domain that specifically binds to an EphA2 receptor, wherein the amino acid sequence of the modified immunoglobulin CH2 domain includes at least one amino acid substitution, addition or deletion in comparison to a wild type immunoglobulin CH2 domain amino acid sequence.

Also provided herein is a heterologous fusion protein including a toxin fused to a modified isolated immunoglobulin CH2 domain that specifically binds to an EphA2 receptor, wherein the amino acid sequence of the modified immunoglobulin CH2 domain includes at least one amino acid substitution, addition or deletion in comparison to a wild type immunoglobulin CH2 domain amino acid sequence.

In addition, the present disclosure provides a pharmaceutical composition including: a modified isolated immunoglobulin CH2 domain that specifically binds to an EphA2 receptor, wherein the amino acid sequence of the modified immunoglobulin CH2 domain includes at least one amino acid substitution, addition or deletion in comparison to a wild type immunoglobulin CH2 domain amino acid sequence, and a pharmaceutical carrier.

Also provided herein is a method for killing a target cell expressing EphA2 receptors in a subject, the method comprising: administering to the subject a fusion protein including a modified isolated immunoglobulin CH2 domain that specifically binds to an EphA2 receptor fused to a toxin, wherein the amino acid sequence of the modified immunoglobulin CH2 domain includes at least one amino acid substitution, addition or deletion in comparison to a wild type immunoglobulin CH2 domain amino acid sequence; and exposing the target cell to an effective amount of the fusion protein, thereby selectively killing the target cell in the subject.

BRIEF DESCRIPTION OF THE DRAWINGS

The present invention will become more fully understood from the detailed description and the accompanying drawings, wherein.

F loop regions: Loop 1, Loop 2, Loop 3, Loop A-B, Loop C-D and Loop E-F. Wild type CH2 domains also comprise seven β sheets, A to G, oriented from the N- to C-terminus. Loops A-B, C-D and E-F are located between β-sheets A and B, C and D, and E and F, respectively. Loops 1, 2 and 3 are located between β-sheets B and C, D and E, and F and G, respectively.

Figure 1:
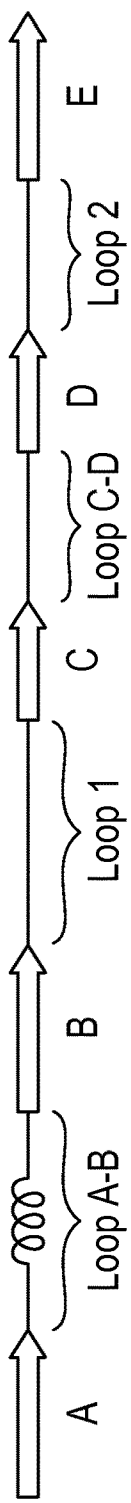
FIG. 1 is a schematic of human wild type immunoglobulin IgG CH2 domain. The numbering refers to the location of the CH2 domain sequence in the human IgG immunoglobulin using EU numbering. See www.imgt.org/IMGTScientificChart/Numbering/Hu_IGHGnber.html, for an explanation of EU numbering and other CH2 domain numbering methodologies, which is herein incorporated by reference in its entirety.
Figure 1:
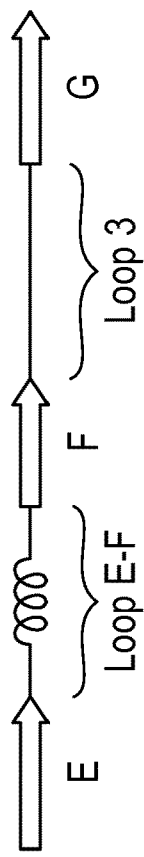
Figure 2:
FIG. 2 is a diagram of the structure of a modified CH2 domain, Loops 1-3 are indicated at the top of the sequence.

In some embodiments, the amino acid sequences of Loops 1, 2 and 3 of the CH2 domains of the present disclosure (also interchangeably referred to herein as L1, L2 and L3, respectively) are modified in comparison to L1, L2 and L3 of a wild type CH2 domain. Amino acids 231-341 of FIG. 1 show a CH2 domain of a wild type IgG human antibody. In this figure, the numbering of the amino acids refers to the location of the CH2 domain in reference to the whole wild type IgG human antibody sequence. The FIG. 1 amino acid sequence is set forth in SEQ ID NO: 1. A diagram of a CH2 domain structure is depicted in FIG. 2.

L1 corresponds to positions 35-44 of SEQ ID NO: 1 (DVSHEDPEVK, SEQ ID NO: 3) or SEQ ID NO: 2 (DVSQEDPDVK, SEQ ID NO: 6), L2 corresponds to positions 63-67 of SEQ ID NO: 1 (EEQYNS, SEQ ID NO: 4) or SEQ ID NO: 2 (ETQYNS, SEQ ID NO: 7) and the L3 corresponds to positions 94-102 of SEQ ID NO: 1 (SNKALPAPI, SEQ ID NO: 5) or SEQ ID NO: 2 (SNKALPAPI, SEQ ID NO: 8).

In some embodiments, the loops of wild type CH2 domains can be 1-2 amino acids longer or shorter than the loop sequences set forth above. The loops may singly or in combination form an antigen binding region, such as an antigen binding region that specifically binds to an EphA2 receptor.

In some embodiments, the framework regions of the immunoglobulin CH2 domains of the present disclosure are also modified. Typically, the term "framework" is conventionally used to refer to amino acid sequences interposed between CDRs (or hypervariable regions) in an intact antibody. Amino acid residues within these framework regions serve to hold the CDRs in an appropriate orientation for antigen binding, and typically form β-sheet structures. As used herein, in the context of a modified immunoglobulin CH2 domain, the term "framework region" refers to amino acid sequences outside of loops 1, 2 and 3; i.e., amino acid sequences interposed between loops 1-2 and between loops 2-3, as well as amino acid sequences N-terminal to loop 1 and C-terminal to loop 3. Wild type CH2 domains contain four framework regions, referred herein as FR1, FR2, FR3 and FR4. The framework regions in CH2 serve to hold loops 1-3 in an appropriate orientation for their usual functions, and also form β-sheet structures.

For example, for the wild type human IgG CH2 domain (SEQ ID NO: 1), framework region 1 is composed of amino acids 1-34 (SEQ ID NO: 9), framework region 2 is composed of 45-62 (SEQ ID NO: 10), framework region 3 is composed of 69-93 (SEQ ID NO: 11) and framework region 4 is composed of amino acids at positions 103-110 (SEQ ID NO: 13). In some embodiments, the framework regions can be 1-2 amino acids longer or shorter than the framework sequences set forth above.

In various embodiments, the disclosed CH2 domain is isolated. As used herein, "isolated" refers to a biological component, such as a CH2 domain, which has been substantially separated or purified away from other biological components from which the component naturally occurs, for example, other biological components of a cell, other antibodies and other antibody domains. CH2 domains that have been "isolated" include nucleic acids and proteins purified by standard purification methods. The term also embraces CH2 domains prepared by recombinant expression in a host cell, as well as chemically synthesized nucleic acids encoding CH2 domains.

Modification of CH2 Domains

One or more loops and/or strands (of the beta sheets, A, B, C, D, E, F, G) of one or more CH2 domains may be modified. As used herein, the terms "modified" or "modification," can include one or more mutations, deletions, additions, substitutions, physical alteration (e.g., cross-linking modification, covalent bonding of a component, post-translational modification, e.g., acetylation, glycosylation, tagging, e.g., His-tags or a combination thereof) or a combination thereof. Modification, e.g., mutation, is not limited to random modification (e.g., random mutagenesis) but includes rational design as well.

Loops

As noted above, in some embodiments, L1, L2 and/or L3 may be modified to specifically bind to an EphA2 receptor. For example, an L1, L2 or L3 amino acid sequence of an isolated immunoglobulin CH2 domain of the present disclosure may include at least one amino acid substitution, addition, or deletion of the amino sequence in comparison to an L1, L2 or L3 amino acid sequence of a wild type CH2 domain. For example, in some embodiments, loops 1, 2 and/or 3 of the modified CH2 domain of the present disclosure may be modified in comparison to loops 1, 2 and/or 3 of the human wild type IgG CH2 domain set forth in SEQ ID NOS: 3-5, respectively. In other embodiments, loops 1, 2 and 3 of the modified CH2 domain of the present disclosure may be modified in comparison to loops 1, 2 and 3 of the macaque wild type IgG CH2 domain set forth in SEQ ID NOS: 6-8, respectively.

In some embodiments, the L1 amino acid sequence may include at least one, two, three, four, five, six, seven, eight, nine or 10 or more amino acid substitutions in comparison to a wild type CH2 domain, such as at position 1, position 2, position, 3, position 4, position 5, position 6, position 7, position 8, position 9 and/or position 10. In other embodiments, the L1 amino acid sequence may include at least one, two, three, four, five, six, seven, eight, nine or 10 or more amino acid deletions in comparison to a wild type CH2 domain. In other embodiments, the L1 amino acid sequence may include at least one, two, three, four, five, six, seven, eight, nine or 10 or more additional amino acids in comparison to a wild type CH2 domain.

In other embodiments, the L2 amino acid sequence is modified in comparison to a wild type L2 amino acid sequence. The modification of L2 may include at least one, two, three, four, five, six, seven, eight, nine or 10 or more amino acid substitutions in comparison to a wild type CH2 domain, such as at position 1, position 2, position, 3, position 4, position 5, position 6, position 7, position 8, position 9 and/or position 10. In other embodiments, the L2 amino acid sequence may include at least one, two, three, four, five, six, seven, eight, nine or 10 or more amino acid deletions in comparison to a wild type CH2 domain. In other embodiments, the L2 amino acid sequence may include at least one, two, three, four, five, six, seven, eight, nine or 10 or more additional amino acids in comparison to a wild type CH2 domain.

In other embodiments, the L3 loop amino acid sequence is modified in comparison to a wild type L3 amino acid sequence. The modification of L3 may include at least one, two, three, four, five, six, seven, eight, nine or 10 or more amino acid substitutions in comparison to a wild type CH2 domain. In other embodiments, the L3 amino acid sequence may include at least one, two, three, four, five, six, seven, eight, nine or 10 or more amino acid deletions in comparison to a wild type CH2 domain. In other embodiments, the L3 amino acid sequence may include at least one, two, three, four, five, six, seven, eight, nine or 10 or more additional amino acids in comparison to a wild type CH2 domain.

In some embodiments, only the L1 amino acid sequence is modified. In other embodiments, only the L2 sequence is modified. In other embodiments, only the L3 amino acid sequence is modified. In various embodiments, the L1 or the L2 sequence is modified. In other embodiments, the L1 and the L2 amino acid sequences are modified. In yet other embodiments, the L1, L2 and L3 amino acid sequences are modified. In some embodiments, the L1 and L3 sequences are modified. In other embodiments, the L2 and L3 sequences are modified.

In some embodiments, the L1 sequence is modified such that it contains 1-6 amino acid substitutions, such as at positions 2-7 of the human wild type L1 amino acid sequence or positions 2-7 of the Macaque L1 amino acid sequence (SEQ ID NOS: 3 or 6, respectively), e.g., positions 2-7 of L1 may be modified with the amino acid sequences described, for example, in SEQ ID NOS: 50-53 or according to residues 2-7 in SEQ ID NOS: 14-15 and 17-21 or residues 2-6 of SEQ ID NO: SEQ ID NO: 16. In other embodiments, the L1 sequence is modified such that it contains 1 deletion, for example, a deletion at position 4 or 5 of the human wild type L1 amino acid sequence (SEQ ID NO: 3) or the L1 Macaque amino acid sequence (SEQ ID NO: 6). In some embodiments, the L1 sequences are modified as set forth in any of SEQ ID NOS: 14-21 or SEQ ID NOS: 85-86 and 94-99.

In some embodiments, the L2 amino acid sequence of the isolated immunoglobulin CH2 domain of the present disclosure is modified to contain 1-6 amino acid substitutions, such as at positions 1-6 of the human wild type L2 amino acid sequence (SEQ ID NO: 4) or the Macaque wild type L2 amino acid sequence (SEQ ID NO: 7). In some embodiments, the L2 amino acid sequence of the modified CH2 domain of the present disclosure is the sequence set forth in SEQ ID NOS: 22-28, such as SEQ ID NOS: 22 or 23.

Framework

In some embodiments, FR1, FR2, FR3 and/or FR4 are modified in comparison to wild type FR1, FR2, FR3 or FR4 regions of a wild type CH2 domain. The modified FR1, FR2, FR3 and FR4 may contain at least one, two, three or four or more deletions, substitutions or additions. In some embodiments, an amino acid sequence of only one of the FR regions may contain a deletion, substitution or addition. For example, FR3 may be modified to include at least one substitution at position 1, e.g., as set forth in SEQ ID NO: 12 or SEQ ID NO: 101. In other embodiments, two or more the FR regions are modified, e.g., FR1 and FR2, FR2, FR3 and FR4, etc.

In various embodiments, the modified, isolated immunoglobulin CH2 domains disclosed herein retain substantially the structure characteristic of a wild type CH2 domain, such as the beta barrel structure of a naturally occurring CH2 domain, i.e., the 3-stranded sheet containing strands C, F, and G, packed against the 4-stranded sheet containing strands A, B, D, and E. Amino acid residues involved in maintaining the beta barrel structure are known in the art, including the residues that form hydrogen bonding, hydrophobic interactions, and the disulfide bond. In specific embodiments, the residues critical to maintaining the beta barrel structure are not modified. In certain embodiments, the framework residues are substantially not modified; for example, not more than 15%, or 10% or 5% of the framework residues are modified in the modified CH2 domains as compared to a wild type CH2 domain. Modifications at or near the terminal regions of a wild type CH2 domain may be more tolerable (i.e., less likely to disrupt the structure or conformation of a wild type CH2 domain) as compared to modifications to other regions.

Standard techniques known to those of skill in the art can be used to introduce mutations in the loop and/or framework regions (e.g., deletions, additions, and/or substitutions) in nucleotide sequences encoding the modified CH2 domains of the present disclosure, including, for example, site-directed mutagenesis and PCR-mediated mutagenesis which results in amino acid substitutions.

In some embodiments, conservative amino acid substitutions are made at one or more predicted non-essential amino acid residues of the loop and/or framework regions of the modified CH2 domains (i.e., amino acid residues that can be modified without abrogating the modified CH2 domain's ability to specifically bind to an EphA2 receptor). A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, a series of variants may be generated that differ by at least one amino acid in their sequence compared with the sequence of the wild type immunoglobulin CH2 domain. Changes may include but are not limited to deletions of an amino acid, additions, and/or substitutions. In generating a library of potential binding molecules, design changes may be focused on the loops. At any one site, variants may be generated that introduce any of the 20 naturally occurring amino acids (or non-natural amino acids), or a more restricted subset of amino acids might be substituted.

Alternatively, in some embodiments, random mutations may be introduced by mutagenesis of the entire molecule, framework regions and loops. Such mutagenesis can be accomplished either in vivo (in a mutagenic host or by addition of exogenous mutagen) or in vitro (by using mutagenic mixtures of precursors and/or by using a DNA polymerase that exhibits reduced or no proofreading nuclease activity). In the case of certain display methods (e.g. phage, CIS, ribosome display), a combination of the two approaches may be employed, synthesizing the initial variants to focus changes within the loops and then allowing random mutagenesis at each round of selection-amplification. Such methods of creating a diverse collection of variant nucleotide sequences to produce variant amino acid sequences are well known in the art. See also the methods for making variant CH2 domains and the CH2 domain libraries described in PCT Publication No. WO 2012/109553, which is herein incorporated by reference in its entirety.

The libraries made in such a way and displayed by any of the established methods available, may be used to isolate individual molecules from that library which bind to a target of interest, e.g., EphA2 receptor. A target molecule, such as an EphA2 receptor, is used to contact a display library to screen for modified CH2 domains that are able to bind to the target molecule. The purified target molecules are presented in either 1) a form that is immobilized on a solid surface, or 2) as soluble molecules in solution. If in solution, they are engineered to bear a simple means for subsequent capture, such as biotin. In the case of cell surface display (e.g. on yeast), the target molecule is tagged fluorescently to enable cell sorting based upon the fluorescent signal due to bound target by the displayed CH2 domain variant. Various methods may be used for detecting the binding of the modified CH2 domain to the target in the sample. Such methods are well known to one of ordinary skill in the art.

Other Modifications

In some embodiments, the modified immunoglobulin CH2 domain comprises a truncation or deletion of the first seven amino acids of the N-terminus of the wild type CH2 domain from which it is derived. Or, in some embodiments, the CH2 domain comprises a deletion of the first amino acid, the first two, the first three, the first four, the first five, the first six, or the first seven amino acids of the N-terminus of the wild type CH2 domain from which it is derived. In some embodiments, the modified CH2 domain comprises a deletion of the first eight, the first nine, or the first ten amino acids of the N-terminus of the wild type CH2 domain from which it is derived. In some embodiments, the modified CH2 domain comprises a deletion of the last four amino acids of the C-terminus of the wild type CH2 domain from which it is derived. In some embodiments, the modified CH2 domain comprises a deletion of the last amino acid, the last two, the last three, the last four, the last five, the last six, the last seven, the last eight, the last nine, or the last ten amino acids of the C-terminus of the wild type CH2 domain from which it is derived. In some embodiments, the modified CH2 domain comprises a deletion at both the N-terminus and the C-terminus of the wild type CH2 domain from which it is derived. For example, in some embodiments, the modified CH2 domain comprises a deletion of the first amino acid, the first two, the first three, the first four, the first five, the first six, or the first seven amino acids of the N-terminus of the wild type CH2 domain from which it is derived and a deletion of the last amino acid, the last two, the last three, the last four, the last five, the last six, the last seven, the last eight, the last nine, or the last ten amino acids of the C-terminus of the wild type CH2 domain from which it is derived. The present disclosure is not limited to the aforementioned examples of deletions. The CH2 domain may comprise other deletions in other regions of the protein. Without wishing to limit the present invention to any theory or mechanism, it is believed that such truncations or deletions (or other modifications) to the molecule may confer a particular property, for example including but not limited to enhanced stability.

In some embodiments, the modified CH2 domain comprises a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. at its N-terminus.

In some embodiments, the modified CH2 domain comprises a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. at its C-terminus, such as set forth in SEQ ID NO: 61 and SEQ ID NOS: 89-93.

In some embodiments, the modified CH2 domain comprises an addition at the N-terminus and at the C-terminus. For example, the CH2 domain may comprise a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. at the N-terminus and a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. at the C-terminus. The additions may include for example, adding a serine, tyrosine, cysteine or lysine residue, for example, to facilitate linking to a linker as described herein below, such as set forth in SEQ ID NO: 61 and SEQ ID NOS: 89 and 91-93.

In some embodiments, one or more portions of the modified CH2 domain or one or more amino acids may be substituted with another peptide or amino acid, respectively. See for example SEQ ID NOS: 54 and 55. In some embodiments, the modified CH2 domain may comprise a tag, for example including but not limited to a His tag.

In further embodiments, the modified CH2 domains that bind EphA2 have additional mutations that further increase stability of the molecule. For example, the molecules can comprise mutations that allow for the formation of non-native disulfide bonds, such as by introducing a pair of amino acid substitutions to replace original residues with cysteine residues. In some examples, a first amino acid substitution is introduced in the N-terminal A strand and the second amino acid substitution is introduced in the C-terminal G strand of the modified CH2 domain of the present disclosure.

For example, the modified CH2 domain may comprise a first amino acid substitution of L12 to C12 and a second amino acid substitution of K104 to C104 (numbered with reference to SEQ ID NO: 1). In other examples, the first amino acid substitution may be V10 to C10 and the second amino acid substitution may be K104 to C104 or K102 to C102 (numbered with reference to SEQ ID NO: 1). See, for example, SEQ ID NOS: 56-59.

In some embodiments, the modified CH2 domain of the present disclosure may be modified to enhance or decrease the affinity and/or avidity the modified CH2 domain has to FcRn, e.g. a human FcRn. As is known in the art, serum half-life of an immunoglobulin is mediated, in part, by the binding of the F, region to the neonatal receptor FcRn. The alpha domain is the portion of FcRn that interacts with the CH2 domain (and possibly CH3 domain) of IgG, and possibly with IgA, and IgD or with the CH3 domain (and possibly CH4 domain) of IgM and IgE. Several studies support a correlation between the affinity for FcRn binding and the serum half-life of an immunoglobulin.

Modifications to the CH2 domain of the present disclosure to enhance or decrease the affinity and/or avidity to FcRn include mutations (amino acid substitutions, deletions, physical modifications to amino acids) of one or more amino acid residues. Modifications may also include insertion of one or more amino acid residues or one or more binding sites (e.g., insertion of additional binding sites for FcRn). A modification may, for example, increase the affinity for FcRn at a lower pH (or higher pH). See, for example, U.S. Patent Application No. 2007/0135620, which is herein incorporated by reference in its entirety).

Examples of amino acid substitutions may include but are not limited to M252Y, S254T, T256E, T307A (in reference to FIG. 1), or a combination thereof. Without wishing to limit the present disclosure to any theory or mechanism, it is believed that one or more of the substitutions M252Y, S254T, T256E, T307A may increase serum half life of the modified CH2 domain by increasing FcRn binding.

In some embodiments, the modified CH2 binding domains, such as a modified macaque IgG immunoglobulin CH2 domain, are deimmunized. As used herein "deimmunized" refers to amino acid sequences carrying one or more amino acid substitutions that (a) reduce an immune response by one to whom a modified CH2 domain, for example, is administered and (b) retains a therapeutically and/or prophylactically effective amount of EphA2 binding activity, for example. Methods for producing deimmunized proteins are known in the art and described, for example, WO2006/082406, WO2004/108158 and WO2004/064724. For example, the method may comprise performing an in silico analysis to predict an epitope in a protein and mutating one or more residues in the predicted epitope to thereby reduce its immunogenicity. The protein is then analyzed, e.g., in silico or in vitro or in vivo to ensure that it retains its ability to bind to EphA2. For example, an epitope that occurs within a loop is not mutated unless the mutation is unlikely to reduce epitope binding. Methods for predicting epitopes are known in the art and described, for example, in Saha et al., BcePred:Prediction of Continuous B-Cell Epitopes in Antigenic Sequences Using Physico-chemical Properties. In Nicosia, Cutello, Bentley and Timis (Eds.) ICARIS 2004, LNCS 3239, 197-204, Springer, 2004. Also for T cell epitopes: Baker MP and Jones TD. Identification and removal of immunogenicity from therapeutic proteins. Current Opinion Drug Discovery and Development. 2007; 10(2):219-227 and WO2006/082406.

EphA2 Receptors

The modified CH2 domain of the present disclosure specifically binds to an EphA2 receptor. The EphA2 receptor may be from any species. In some embodiments, the EphA2 receptor is from a mammal, e.g., a dog, cat, sheep, goat, rat, mouse, macaque, baboon, or a human. Typically, the EphA2 receptor is from a mouse, macaque or a human.

As used herein "specifically binds" refers to the preferential association of a binding agent, such as a modified CH2 domain, in whole or part, with a cell or tissue bearing the target of that binding agent and not to cells or tissues lacking a detectable amount of that target. It is recognized that a certain degree of non-specific interaction may occur between a molecule and a non-target cell or tissue. Nevertheless, specific binding may be distinguished as mediated through specific recognition of an antigen. Specific binding typically results in greater than 2-fold, such as greater than 5-fold, greater than 10-fold, or greater than 100-fold increase in amount of bound molecule (per unit time) to a cell or tissue bearing the target as compared to a cell or tissue lacking the target, respectively. Specific binding to a protein under such conditions requires a molecule that is selected for its specificity for a particular protein. A variety of immunoassay formats are appropriate for selecting molecules specifically reactive with a particular protein. For example, solid-phase ELISA immunoassays are routinely used.

As used herein, the term "EphA2 receptor" refers to a tyrosine kinase belonging to the Eph receptors family, and comprising, for example, an amino sequence as in Genbank Accession Nos. NM_004431.3, GI:296010835 (human EphA2), herein incorporated by reference in its entirety, NM_010139.3, GI:342187227 (murine EphA2), herein incorporated by reference in its entirety or NM_001108977.1 GI:157822928 (rat EphA2), herein incorporated by reference in its entirety. In some embodiments, the modified CH2 domains specifically bind to a human EphA2 receptor.

As is known in the art, the Eph receptors comprise several distinctive domains required for their signaling capabilities. The extracellular domain contains an ephrin ligand-binding domain in its N-terminal region, followed by a cysteine-rich region and two fibronectin type-III repeats. The intracellular region comprises the signaling components which include a tyrosine kinase domain, a SAM (Sterile Alpha Motif) domain, and a PDZ (Postsynaptic density protein, Disks large, Zona occludens)-binding motif. Both SAM and the PDZ domains have been shown to mediate protein-protein interactions.

GPI-anchored plasma membrane proteins ephrin-A1 to ephrin-A5 are known as EPHA2 ligands. The ligand binding to EPHA2 activates the tyrosine kinase domain and phosphorylates tyrosine residues present in the EPHA2 intracellular region, resulting in signal transduction within the cell. It has also been reported that EPHA2 bound with the ligand is internalized into the cell through endocytosis and is eventually degraded by a proteasome.

In some embodiments, the modified CH2 domains described herein are capable of inhibiting one or more of the biological activities of a target molecule, such as an EphA2 receptor. Such antagonists may act by interfering with the binding of a receptor to a ligand, by decreasing EphA2 phosphorylation that could be induced by a ligand, and/or by inhibiting the intracellular pathways that are induced by the binding of such ligand, and/or by inhibiting the homo/hetero-oligomerization of EphA2 receptors. The antagonist may completely block receptor-ligand interactions or may substantially reduce such interactions. Accordingly, the modified CH2 domains of the present invention may act as antagonists (e.g. act as neutralizing antibodies) that bind to EphA2 receptor, EphA2 ligand or a complex of an EphA2 receptor and EphA2 ligand. In other embodiments, the modified CH2 domains of the present disclosure stimulate phosphorylation of the EphA2, thereby triggering degradation of said protein.

In some embodiments, the modified CH2 domains of the present specifically bind to the EphA2 receptor. In some embodiments, the modified CH2 domains specifically bind to the extracellular domain of the EphA2 receptor.

Modified CH2 domains, capable of specifically binding the EphA2 receptor, typically, the extracellular domain of the EphA2 receptor, are herein provided, e.g. the modified CH2 domains designated as E10, H6, D2, G7, B6, B11, F4.1, C5, D9 and E3 set forth as SEQ ID NOS: 29-38. In other embodiments, the modified CH2 domains, capable of specifically binding the EphA2 receptor, typically, the extracellular domain of the EphA2 receptor, include for example, the modified CH2 domains set forth in SEQ ID NOS: 89-93.

Also provided herein are isolated modified immunoglobulin CH2 domains that specifically bind to an EphA2 receptor, wherein the modified CH2 domains competitively inhibits binding of an isolated immunoglobulin CH2 domain selected from the group consisting of E10, D2, G7, B6, B11, B4.1, C5, D9, and E3.

In a specific embodiment, the disclosure encompasses modified CH2 domains that reduce the binding of E10, H6, D2, G7, B6, B11, B4.1, C5, D9 and E3 to an EphA2 receptor by at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, 25% to 50%, 45 to 75%, or 75 to 99% relative to a control such as PBS in the competition assays well known in the art.

For example, an ELISA competition assay may be performed in the following manner: recombinant EphA2 is prepared in PBS at a concentration of 10 µg/ml. 100 µl of this solution is added to each well of an ELISA 98-well microtiter plate and incubated overnight at 4-8° C. The ELISA plate is washed with PBS supplemented with 0.1% Tween to remove excess recombinant EphA2. Non-specific protein-protein interactions are blocked by adding 100 µl of bovine serum albumin (BSA) prepared in PBS to a final concentration of 1%. After one hour at room temperature, the ELISA plate is washed. Unlabeled competing CH2 domains are prepared in blocking solution at concentrations ranging from 1 µg/ml to 0.01 µg/ml. Control wells contain either blocking solution only or control antibodies at concentrations ranging from 1 µg/ml to 0.01 µg/ml. Test antibody labeled with horseradish peroxidase is added to competing antibody dilutions at a fixed final concentration of 1 µg/ml. 100 µl of test and competing CH2 domain mixtures are added to the ELISA wells in triplicate and the plate is incubated for 1 hour at room temperature. Residual unbound CH2 domain is washed away. Bound test CH2 domain is detected by adding 100 µl of horseradish peroxidase substrate to each well. The plate is incubated for 30 min. at room temperature, and absorbance is read using an automated plate reader. The average of triplicate wells is calculated. CH2 domains which compete well with the test antibody reduce the measured absorbance compared with control wells.

The strength of binding between a binding site (X) and a ligand (Y), for example, between a modified CH2 domain of the present disclosure and an EphA2 receptor, may be characterized by the dissociation constant (Kd). Kd is the concentration of Y that is required to occupy half of the binding sites of X present in a solution. A lower (Kd) indicates a stronger or higher-affinity interaction between X and Y and a lower concentration of ligand is needed to occupy the sites. Methods for determining binding affinity are well known in the art.

In some embodiments, the Kd resulting from binding between a modified CH2 domain and an EphA2 receptor or extracellular domain thereof, is less than $1\times10^{-2}$M, less than $1\times10^{-3}$M, less than $1\times10^{-4}$M, less than $1\times10^{-5}$M, less than $1\times10^{-6}$M, less than $1\times10^{-7}$M, less than $1\times10^{-8}$M, less than $1\times10^{-9}$M, less than $1\times10^{-10}$M, less than $1\times10^{-11}$M, less than $1\times10^{-12}$M, less than $1\times10^{-13}$M, less than $1\times10^{-14}$M or less than $1\times10^{-15}$M.

Immunoconjugates

In some embodiments, the modified CH2 domains described herein may be joined to a second molecule to form an immunoconjugate, wherein the second molecule is, for example, a detectable moiety, a toxin, an epitope binding protein or a small molecule. The terms "linking", "joining," or "bonding" refer to making two polypeptides into one continuous polypeptide molecule, or to covalently attaching the modified CH2 domain of the present disclosure to the second molecule.

Detectable Moiety

For example, the modified CH2 domains may be joined to a detectable moiety for use in in vivo or in vitro imaging, wherein the labeled, modified CH2 domain is administered to a subject, such as into the bloodstream, and the presence and location of the labeled CH2 domain in the host is assayed. In some embodiments, imaging is useful in the staging and treatment of malignancies. The modified CH2 domain of the present disclosure may be labeled with any moiety that is detectable in a host, whether by PET/CT imaging or other detection means known in the art.

The label can be any detectable moiety that is capable of producing, either directly or indirectly, a detectable signal. For example, the label may be a detectable radioisotope, e.g., $^{64}$Cu, $^{67}$Cu, $^{90}$Y, $^{111}$In, $^{124}$I, $^{125}$I, $^{131}$I, $^{137}$Cs, $^{186}$Re, $^{211}$At, $^{212}$Bi, $^{213}$Bi, $^{223}$Ra, $^{241}$Am, $^{244}$Cm and $^{99m}$Tc-MDP, a fluorescent compound, e.g., fluorescein phycoerythrin, phycocyanin, allophycocyanin, o-phthaldehyde and fluorescamine); chemiluminescent compound (e.g., fluorescein isothiocyanate, rhodamine), an enzyme label (e.g., luciferase, alkaline phosphatase, beta-galactosidase and horseradish peroxidase), an imaging agent (e.g., Tc-m99 and indium ($^{111}$In) and/or a metal ion (e.g., gallium and europium). In some embodiments, bifunctional chelators e.g., MeCOSar are labeled with radioisotopes, e.g., $^{64}$Cu.

Toxins, Epitope Binding Proteins, Small Molecules

In other embodiments, the modified isolated immunoglobulin CH2 domain is fused to a toxin to form a heterologous fusion protein. As used herein, "fusion protein" refers to a hybrid protein, which consists of two or more proteins, or fragments thereof, linked together covalently. A fusion protein may be "heterologous", i.e., comprising two or more peptides or proteins from different animals, origins, or species.

In some embodiments, the toxins, which may be bound to the modified CH2 domain of the present disclosure include, but are not limited to, abrin, ricin, *Pseudomonas* exotoxin (PE, such as PE18, PE24, and PE38), diphtheria toxin (DT), botulinum toxin, saporin, restrictocin or gelonin, or modified toxins thereof. Other cytotoxic agents that may be attached to the modified CH2 domain include cytolytic peptides.

In some embodiments, the toxin is a fungal ribonuclease, for example, α-sarcin or a deimmunized α-sarcin. A deimmunized toxin is one that (a) reduces the anti-toxin immune response by one to whom the toxin is administered, and (b) retains a therapeutically and/or prophylactically effective amount of toxin activity. Methods for preparing deimmunized α-sarcin are well known in the art, as disclosed, for example, in WO 2014/158770, which publication is hereby incorporated by reference in its entirety. By way of example, the deimmunized α-sarcin can have an amino acid sequence as set forth in the following table:

| SEQ ID NO: | Variant |
|---|---|
| 62 | Q10X (X = K or A)<br>AVTWTCLND<u>X</u> KNPKTNKYET KRLLYNQNKA ESNSHHAPLS DGKTGSSYPH WFTNGYDGDG KLPKGRTPIK FGKSDCDRPP KHSKDGNGKT DHYLLEFPTF PDGHDYKFDS KKPKENPGPA RVIYTYPNKV FCG<u>I</u>IAHTKE NQGELKLCSH |

| SEQ ID NO: | Variant |
|---|---|
| 63 | N16X(X = R, K or A)<br>AVTWTCLNDQ KNPKTXKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NQGELKLCSH |
| 64 | Y18X (X = K or R)<br>AVTWTCLNDQ KNPKTNKXET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NQGELKLCSH |
| 65 | K139X (X = D or E)<br>AVTWTCLNDQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTXE NQGELKLCSH |
| 66 | E140D<br>AVTWTCLNDQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKD NQGELKLCSH |
| 67 | Q142X (X = N, T, or E)<br>AVTWTCLNDQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NXGELKLCSH |
| 68 | Q10K + K139X (X = D or E)<br>AVTWTCLNDK KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTXE NQGELKLCSH |
| 69 | N16R + K139X (X = D or E)<br>AVTWTCLNDQ KNPKTRKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTXE NQGELKLCSH |
| 70 | Y18$X_1$ ($X_1$ = K or R) + K139$X_2$ ($X_2$ = D or E)<br>AVTWTCLNDQ KNPKTNK**$X_1$ET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHT$X_2$**E NQGELKLCSH |
| 71 | Q10K + Q142T<br>AVTWTCLNDK KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 72 | Q10K + K139D + Q142T<br>AVTWTCLNDK KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTDE NTGELKLCSH |
| 73 | Q10K + K139E + Q142T<br>AVTWTCLNDK KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTEE NTGELKLCSH |
| 74 | N16R + K139D + Q142T<br>AVTWTCLNDQ KNPKTRKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTDE NTGELKLCSH |
| 75 | N16R + K139E + Q142T<br>AVTWTCLNDQ KNPKTRKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTEE NTGELKLCSH |

-continued

| SEQ ID NO: | Variant |
|---|---|
| 76 | D9T + Q142T<br>AVTWTCLNTQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 77 | Q10A + Q142T<br>AVTWTCLNDA KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 78 | P13I + Q142T<br>AVTWTCLNDQ KNIKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 79 | T15G + Q142T<br>AVTWTCLNDQ KNPKGNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 80 | Y18K + Q142T<br>AVTWTCLNDQ KNPKTNKKET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 81 | N16A+ Q142T<br>AVTWTCLNDQ KNPKTAKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 82 | Y18R + Q142T<br>AVTWTCLNDQ KNPKTNKRET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NTGELKLCSH |
| 83 | T15G + Q142G<br>AVTWTCLNDQ KNPKGNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE NGGELKLCSH |
| 84 | T15G + E140D<br>AVTWTCLNDQ KNPKGNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKD NQGELKLCSH |

In other embodiments, the modified isolated immunoglobulin CH2 domain is fused to one or more proteins comprising a paratope. Accordingly, the CH2 domain of the present disclosure may be modified to be specific for one, two, three or more targets, e.g. EphA2 and a T cell-specific epitope, a natural killer (NK) cell-specific epitope (e.g., Fc gammaR 111a/CD16A) etc In such embodiments, a bispecific modified CH2 domain of the present disclosure, for example, recruits an effector cell, such as a T cell, to an aberrant target cell, such as a cell overexpressing EphA2, resulting in the immune effector cell being in close vicinity to the target cell, such that the effector cell can directly kill, or indirectly initiate the killing of the aberrant target cell to which it is recruited. In some embodiments, the T cell-specific epitope is CD3.

In other embodiments, the modified isolated immunoglobulin CH2 domain of the present disclosure is linked to a small molecule. As used herein a "small molecule" refers to a beneficial agent, usually synthesized by organic chemistry and having a low molecular weight, e.g. about 500-900 daltons. Generally, a small molecule is an effector of a specific protein or nucleic acid, altering the activity of the protein or nucleic acid. Examples of small molecules include but are not limited to cytotoxic agents, e.g., compound classes such as the auristatins, maytansinoids and pyrrolobenzodiazepines. See, for example, Jeffrey et al., "A potent anti-CD70 antibody-drug conjugate containing a dimeric pyrrolobenzodiazapene drug with site-specific conjugation technology", *Bioconjugate Chem.*, 2013, 24:1256-1263, which is incorporated herein by reference in its entirety and Smaglo et al., "The development of immunoconjugates for targeted cancer therapy," *Nature Reviews Oncology*, 2014, 11:637-648.

Linkage

In some embodiments, the N-terminus of the detectable moiety, toxin, protein comprising a paratope or small molecule is linked to the C-terminus of the modified CH2 domain. In some embodiments, the N-terminus of the detectable moiety, toxin, protein comprising a paratope or small molecule is linked to the N-terminus of the CH2 domain. In some embodiments, the C-terminus of the detectable moiety, toxin, protein comprising a paratope or small molecule is linked to the C-terminus of the CH2 domain. In some embodiments, the N-terminus of the CH2 domain is linked to the C-terminus of the detectable moiety, toxin, protein comprising a paratope or small molecule. In some embodiments, the N-terminus of the CH2 domain is linked to the N-terminus of the detectable moiety, toxin, protein comprising a paratope or small molecule. In some embodiments, the C-terminus of the modified CH2 domain is linked to the C-terminus of the detectable moiety, toxin, protein comprising a paratope or small molecule.

In some embodiments, a linker can optionally be inserted between the modified CH2 domain and the detectable moiety, toxin, protein comprising a paratope or small molecule. Linkers and linker technology are well known in the art. Examples of linkers include peptides of various amino acid lengths and/or sequences. In some embodiments, the linker is between 0 to 10 amino acids in length. In some embodiments, the linker is between 0 to 15 amino acids in length. In some embodiments, the linker is between 0 to 20 amino acids in length. In some embodiments, the linker is between 1 to 10 amino acids in length. In some embodiments, the linker is between 1 to 15 amino acids in length. In some embodiments, the linker is between 1 to 20 amino acids in length. In some embodiments, the linker is between 2 to 20 amino acids in length. In some embodiments, the linker is between 3 to 20 amino acids in length. In some embodiments, the linker is between 4 to 20 amino acids in length. In some embodiments, the linker is between 5 to 10 amino acids in length. In some embodiments the linker is between 10 to 15 amino acids in length. In some embodiments, the linker is between 15 to 20 amino acids in length. In some embodiments, the linker is more than 20 amino acids in length. The optimal lengths may vary to match the spacing and orientation of the specific target antigen(s), minimizing entropy but allowing effective binding of multiple antigens.

The linker can be attached to the individual modified CH2 domain at any appropriate location. Examples of where a linker may attach onto the modified CH2 domain include the following location on the modified CH2 domain: the C-terminus, the N-terminus or a cysteine preceding or following the C-terminus or N-terminus of the modified CH2 domain, such as set forth in SEQ ID NOS: 89-93.

The linker may be encoded for in the recombinant nucleic acid that encodes the immunoconjugate, e.g. fusion protein. In some embodiments, the linker may be covalently bonded (e.g., cross-linked) to a portion of an immunoconjugate. The linkers may be covalent or very tight non-covalent linkages; chemical conjugation or direct gene fusions of various amino acid sequences, e.g., those (a) rich in Glycine Serine, Proline, Alanine.

In some embodiments, the linker comprises a non-peptide component (e.g., a sugar residue, a heavy metal ion or a chemical agent such as a therapeutic chemical agent). Classes of commonly used cleavable linkers include hydrazone and hydrazine linkers, disulfide linkers (including N-succinimidyl-4-(2-pyridyldithio)pentanoate (SPP), N-succinimidyl-4-(2-pyridyldithio)butyrate (SPDB), 4-(4"-acetylphenoxy)butanoic acid (AcBut), dipeptides valine-citrulline (Val-Cit), valine-alanine (Val-Ala), and phenylalanine-lysine (Phe-Lys), the dissolving linker technology of Mersana and protease susceptible linkers of CytomX. Commonly used non-cleavable linkers include: amide moieties, succinimidyl-4-[N-maleimidomethyl]cyclohexane-1-carboxylate (SMCC), maleimidocaproyl (MC), the dPEG linkers, and pyridinyl-2-disulfanyl linkers.

In other embodiments, the linker comprises polyethylene glycols (PEGs), e.g., discrete PEGs (dPEG), etc. See, for example, Dennis et al., 2002, *Journal of Biological Chemistry* 33:238390, discrete PEGs from Quanta BioDesign, Ltd., Powell, Ohio, which is herein incorporated by reference in its entirety. A PEG (dPEG) may be bound by a variety of mechanisms, e.g., via chemical treatments and/or modification of the protein structure, sequence, etc. (see, for example, Ashkenazi et al., 1997, *Current Opinions in Immunology* 9:195-200; U.S. Pat. No. 5,612,034; U.S. Pat. No. 6,103,233).

In some embodiments, the PEG (dPEG) is between about 200 to 10,000 daltons. In some embodiments, the (dPEG) is between about 600 to 10,000 daltons. In some embodiments, the PEG (dPEG) is between about 700 to 10,000 daltons. In some embodiments, the (dPEG) is between about 800 to 10,000 daltons. In some embodiments, the (dPEG) is between about 900 to 10,000 daltons. In some embodiments, the (dPEG) is between about 200 to 12,000 daltons.

In some embodiments, the PEG (dPEG) may be linked to a linkage site, such as at least one of a serine, tyrosine, cysteine, or lysine or a glycosylation site of the modified CH2 domain. The PEG (dPEG) may be bound to the immunoconjugate, e.g., a fusion protein (e.g., modified CH2 domain) through a reactive sulfhydryl by incorporating a cysteine at the end of the modified CH2 domain to form, e.g. CH2-dPEG-toxin, detectable moiety, protein comprising a paratope or a small molecule.

In some embodiments, the linkage site is an N-terminal serine, tyrosine, cysteine, or lysine. In other embodiments, the linkage site is a C-terminal serine, tyrosine, cysteine, or lysine. In some embodiments, the linkage site is a serine, tyrosine, cysteine, or lysine found within the modified CH2 domain, not necessarily a terminal residue. In some embodiments, a tyrosine, cysteine, serine, or lysine is added to the N-terminus and/or C-terminus of the CH2 scaffold for the purpose of the linkage of the PEG (dPEG). Alternatively, a PEG (dPEG) may be linked to an existing tyrosine, cysteine, serine, or lysine at a terminus or within the modified CH2 domain. In some embodiments, the CH2-PEG (dPEG) is then further linked to the detectable moiety, toxin, protein comprising a paratope or small molecule.

In various embodiments, the PEG (dPEG) is linked to a glycosylation site. In some embodiments, the glycosylation site is a natural glycosylation site. In some embodiments, the glycosylation site is a new/modified glycosylation site, for example an asparagine N-glycosylation site may be added to the modified CH2 domain. A PEG (dPEG) may be attached at a glycosylation site using methods including enzymatic digestion and expression with an appropriate expression system (e.g., *Pichia* GlycoSwitch® Man5 strain). In some embodiments, the dPEG is attached to a natural Man5 structure or alternatively a GnMan5 structure, a GalGnMan5 structure, a GnMan3 structure, a GalGnMan3 structure, a Gn2Man3 structure, a Gal2Gn2Man3, etc. Further methods for using PEG and linkage arrangements of CH2 domains, detectable moieties, toxins, proteins comprising paratopes or small molecules are well known in the art, see, for example, PCT Publication No. WO 2013/119903, which is herein incorporated by reference in its entirety.

In some embodiments, the linker is a hinge component. For example, the hinge component set forth in SEQ ID NO: 60 may be linked to the N-terminus of the FR1 region of a modified CH2 domain. Other linkers for fusion proteins are also described in PCT Publication No. WO 2013/119903, which is herein incorporated by reference in its entirety.

Pharmaceutical Compositions

The modified CH2 domains and fusion proteins of the present disclosure are useful as pharmaceutical agents, particularly, as pharmaceutical compositions intended for cancer treatment. Any cancer that expresses the EphA2 receptor can be treated using these pharmaceutical compositions. Examples of cancer types can include, but are not limited to, breast cancer, melanoma, ovarian cancer, lung cancer, gliomas, bladder cancer, prostate cancer, esophageal cancer, renal cancer, colon cancer and vulvar cancer.

In some embodiments, the compositions comprise a modified CH2 domain or a fusion protein comprising a modified CH2 domain linked to a toxin as discussed above and a pharmaceutical carrier. The pharmaceutical carrier (vehicles) may be conventional, but are not limited to conventional carriers (vehicle). For example, E. W. Martin, Remington's Pharmaceutical Sciences, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21st Edition (2006) describe compositions and formulations suitable for pharmaceutical delivery of one or more therapeutic compounds or molecules and additional pharmaceutical agents. In some embodiments aqueous pharmaceutical compositions suitable for long-term storage of polypeptides containing an Fc domain of an immunoglobulin may be used, such as described in U.S. Pat. No. 7,648,702, which is hereby incorporated by reference in its entirety.

Pharmaceutical compositions may comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), amino acids (e.g., arginine, cysteine, histidine, glycine, serine, lysine, alanine, glutamic acid, proline), sodium chloride, potassium chloride, sodium citrate, sucrose, glucose, mannitol, lactose, glycerol, xylitol, sorbitol, maltose, inositol, trehalose, bovine serum albumin (BSA), albumin (e.g., human serum albumin, recombinant albumin), dextran, PVA, hydroxypropyl methylcellulose (HPMC), polyethyleneimine, gelatin, polyvinylpyrrolidone (PVP), hydroxyethylcellulose (HEC), polyethylene glycol (PEG), ethylene glycol, dimethylsulfoxide (DMSO), dimethylformamide (DMF), hydrochloride, sacrosine, gamma-aminobutyric acid, Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof.

In some embodiments, the pharmaceutical compositions may comprise propellants (e.g., hydrofluoroalkane (HFA)) for aerosol delivery. In some embodiments, the pharmaceutical compositions of the present disclosure may be formulated as described in U.S. Pat. No. 5,192,743 that form a gel when reconstituted and which can improve stability of a protein of interest (e.g., for storage).

Pharmaceutical compositions may be appropriately constructed for some or all routes of administration, for example topical administration (including inhalation and nasal administration), oral or enteral administration, intravenous or parenteral administration, transdermal administration, epidural administration or the like. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, a parenteral formulation may comprise injectable fluids that include pharmaceutically and physiologically acceptable fluids such as water, physiological saline, balanced salt solutions, aqueous dextrose, glycerol or the like as a vehicle. As a non-limiting example, the formulation for injectable trastuzumab includes L-histidine HCl, L-histidine, trehalose dihydrate and polysorbate 20 as a dry powder in a glass vial that is reconstituted with sterile water prior to injection. Other formulations of antibodies and proteins for parenteral or subcutaneous use are well known in the art and may be used with the modified CH2 domains and fusion proteins of the present disclosure.

For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The aforementioned pharmaceutical compositions and protein modifications to increase protein stability can be applied as described in U.S. Patent Application 2009/032692, which is herein incorporated by reference in its entirety.

Therapeutic Methods

The present invention is further directed to treating a disease associated with EphA2 overexpression. As used herein, "treatment" or "treating" refers to arresting or inhibiting, or attempting to arrest or inhibit, the development or progression of a disease and/or causing, or attempting to cause, the reduction, suppression, regression, or remission of a disease and/or a symptom thereof. As would be understood by those skilled in the art, various clinical and scientific methodologies and assays may be used to assess the development or progression of a disease, and similarly, various clinical and scientific methodologies and assays may be used to assess the reduction, regression, or remission of a disease or its symptoms. "Treatment" refers to both therapeutic treatment and prophylactic or preventative measures. Those in need of treatment include those who already have the disease, as well as those with a propensity or predisposition for the disease and those in whom the disease is to be prevented. In at least one embodiment, the disease being treated is cancer, such as described above.

As used herein, a "disease associated with EphA2 overexpression" includes, but is not limited to a variety of cancers, including the cancers described herein.

The modified CH2 domains of the present disclosure and the fusion proteins described above may be administered to a subject. In some embodiments, the subject is a mammal including a cat, dog, horse, sheep, goat, rat, mouse, baboon, macaque or human. Preferably, the subject is a human.

In various embodiments, a therapeutically effective dose of the modified CH2 domains or fusion proteins described herein is administered. As used herein "a therapeutically effective dose" is an amount which eliminates or reduces the patient's tumor burden, or which prevents or reduces the proliferation of metastatic cells. The dosage will depend on many parameters, including the nature of the tumor, patient history, patient condition, the possible co-use of other oncolytic agents, and methods of administration.

Methods of administration include injection (e.g., parenteral, subcutaneous, intravenous, intraperitoneal, etc.). Typical dosages may range from about 0.01 to about 20 mg/kg, and more particularly from about 0.1 to about 10 mg/kg. Other methods of administration include oral and transdermal.

In some embodiments, the modified CH2 domains and fusion proteins can be delivered in a controlled release system. Such methods may include the use of a pump for administration, such as use of an intravenous drip. In another embodiment, a controlled release system can be placed in the proximity of the therapeutic target, such as a tumor, requiring only a fraction of the dose required if dosed systemically.

In various embodiments, administration is locally confined to a single cell or tissue and/or is systemically administered in the subject. It may be desirable to administer the modified CH2 domains and fusion proteins described herein locally to the area in need of treatment, such as areas including one or more tumor. This method of administration may be achieved by, for example, and not by way of limitation, local infusion during surgery, topical application such as in conjunction with a wound dressing after surgery, injection, catheter, or via an implant or porous membrane.

In some embodiments, the present invention is directed a method for killing a target cell expressing EphA2 receptors, the method comprising administering to a subject in need thereof a fusion protein as described herein, exposing the target cell to an effective amount of the fusion protein, thereby selectively killing the target cell in the subject. In some embodiments, the modified CH2 domain of the fusion protein is capable of being internalized into the cells.

As used herein, "selectively killing" means that the fusion protein preferentially associates in whole or in part with a cell or tissue bearing the EphA2 receptor, such as the extracellular domain of the EphA2 receptor and not to cells or tissues lacking the EphA2 cell receptor. As noted above, EphA2 has been shown to have little to no appreciable expression in normal tissues, but may be highly expressed in tumors. Accordingly, in some embodiments, the fusion protein selectively kills tumor cells, but does not kill normal cells.

In some embodiments, the fusion protein is formulated into a pharmaceutical composition. The pharmaceutical composition comprises the fusion protein and a pharmaceutically acceptable carrier, such as described above. The subject may be a mammal or any species of mammal as described herein. In some embodiments, the subject is a human.

In some embodiments, the target cell is a cancer cell, including, for example, a cancer cell selected from the group consisting of lung, colon, rectum, breast, ovary, prostate gland, head, neck, bone, kidney, liver, skin and vulva.

Exposure of the target cells to the fusion protein may be carried out by any of a number of routes, including without limitation, intravenous, intraperitoneal, subcutaneous, intramuscular and intralymphatic. As described herein, the fusion protein may be one in which the modified CH2 domain and the toxin are covalently associated.

The term "effective amount" as used herein means that amount of fusion protein or pharmaceutical composition comprising the fusion protein necessary to achieve the desired specific effect, for example killing a target cell and/or in amelioration of a specific disease state.

Furthermore, it would be understood by those skilled in the art that the therapeutic methods described would not only apply to treatment in a subject, but could be applied to cell cultures, organs, tissues, or individual cells in vivo, ex vivo or in vitro.

It would also be understood by a skilled artisan how to use the modified CH2 domains and fusion proteins of the present invention for diagnostic purposes without undue experimentation based on the teachings provided throughout the specification.

Examples

Example 1. Library Construction and Screening

A. First Generation Libraries

Four first generation libraries were designed using three randomized loops of the CH2 domain, Loop 1, Loop 2 and Loop 3. The libraries were built using trinucleotide primers, where each codon was replaced by an equimolar mix of codons encoding the selected amino acids. As shown in Table 1, selected amino acids in the sequence of the loops were targeted for replacement with alternate amino acids. The numbering of the sequences corresponds to the residues set forth in FIG. 1.

TABLE 1

First generation libraries showing which residues were randomized in each loop.

| Library code | Loop 1 | Loop 2 | Loop 3 | Theoretical diversity |
|---|---|---|---|---|
| #13 | Ser267→Asp270 | / | / | 2 × 10e4 |
| #15 | / | Glu293→Thr299 | / | 4 × 10e7 |
| #16 | / | / | Lys326→Ala330 | 2.5 × 10e5 |
| #17 | Ser267→Asp270 | Glu293→Thr299 | / | 8 × 10e11 |

The four libraries were cloned in the phagemid vector pIFF6 fused in frame with the minor coat protein pIII for the display on the surface of the filamentous phage M13. Phagemid vector pIFF6 is derived from the pC89 vector and contains the coding sequence for the capsid protein pIII in place of pVIII. After electroporation in TOP10F' cells, a number of independent clones sufficient to cover the entire diversity of the libraries were collected and 100 clones for each library underwent sequencing to confirm the correct reading frame and the expected sequences pattern. The 4 libraries were individually rescued, purified and titrated, then used in a pool to select against the EphA2 receptor. After three rounds of selection on coated mEphA2-Fc, the phage pool supernatants coming from the three rounds of selection were tested in DElisa assay on coated mEphA2 to assess the enrichment for binding ability to the target. At the third round of selection, the pool of selected clones increased the capability of binding to mEphA2. To identify the single positives, 192 clones were individually rescued and analyzed by ELISA on coated mEphA2. All 95 clones identified as positives were sequenced and seven variants were identified.

Despite all three loops being engineered separately in individual libraries, the selected clones were all isolated from the loop 2 library (library #15).

TABLE 2

Sequences of loop 2 clones selected for EphA2 binding.

| Clone | Loop 2 | SEQ ID NO: |
|---|---|---|
| H6 | RVDPLGG | 43 |
| E10 | QYDPLYG | 44 |
| D2 | QLDPLYG | 45 |
| B8 | GYYALGG | 46 |
| B11 | SYYALGG | 47 |
| H3 | AYYALGG | 48 |
| A5 | ERYVSYV | 49 |

Two strong consensus motifs can be observed in the selected binders: the first, x-x-D-P-L-x-G (SEQ ID NO: 39) in clones H6, E10 and D2 and secondly, x-Y-Y-A-L-G-G (SEQ ID NO: 40) in clones B8, B11 and A9. Clone A5 does not share consensus with the other sequences. The different sequence motifs may reflect binding to alternative epitopes.

Figure 3:
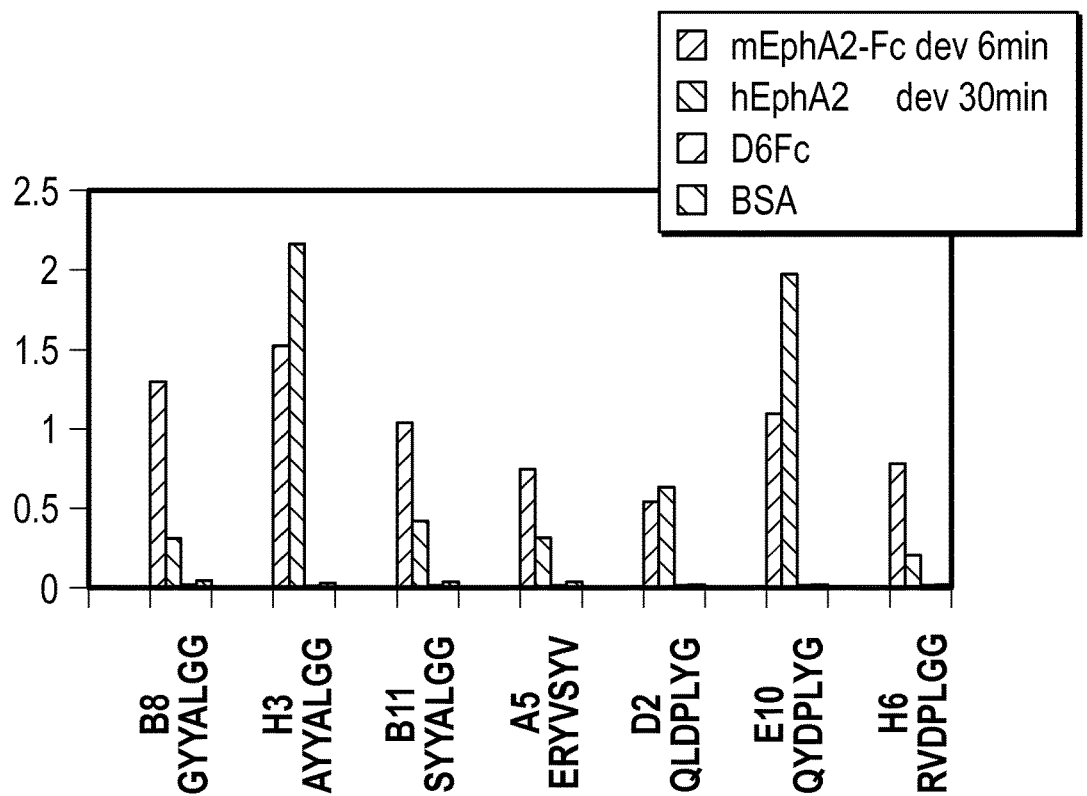
FIG. 3 shows the results of a phage ELISA on mouse EphA2, human EphA2, D6-Fc (control) and BSA (control) with individual positives clones B8 (SEQ ID NO: 46), H3 (SEQ ID NO: 48), B11 (SEQ ID NO: 47), A5 (SEQ ID NO: 49), D2 (SEQ ID NO: 45), E10 (SEQ ID NO: 44) and H6 (SEQ ID NO: 43).

Binding capability and specificity of the seven unique clones were confirmed by ELISA assay, coating mEphA2-Fc protein, hEphA2, D6-Fc and BSA. All the isolated clones specifically bind both human and murine EphA2 recombinant protein. None of the isolated clones recognize the Fc domain linked to the selector mEphA2 or unrelated proteins, such as BSA or D6-Fc. The clones H3 and E10 seemed to bind to human EphA2 more strongly than the other variants. See FIG. 3.

Figure 4:
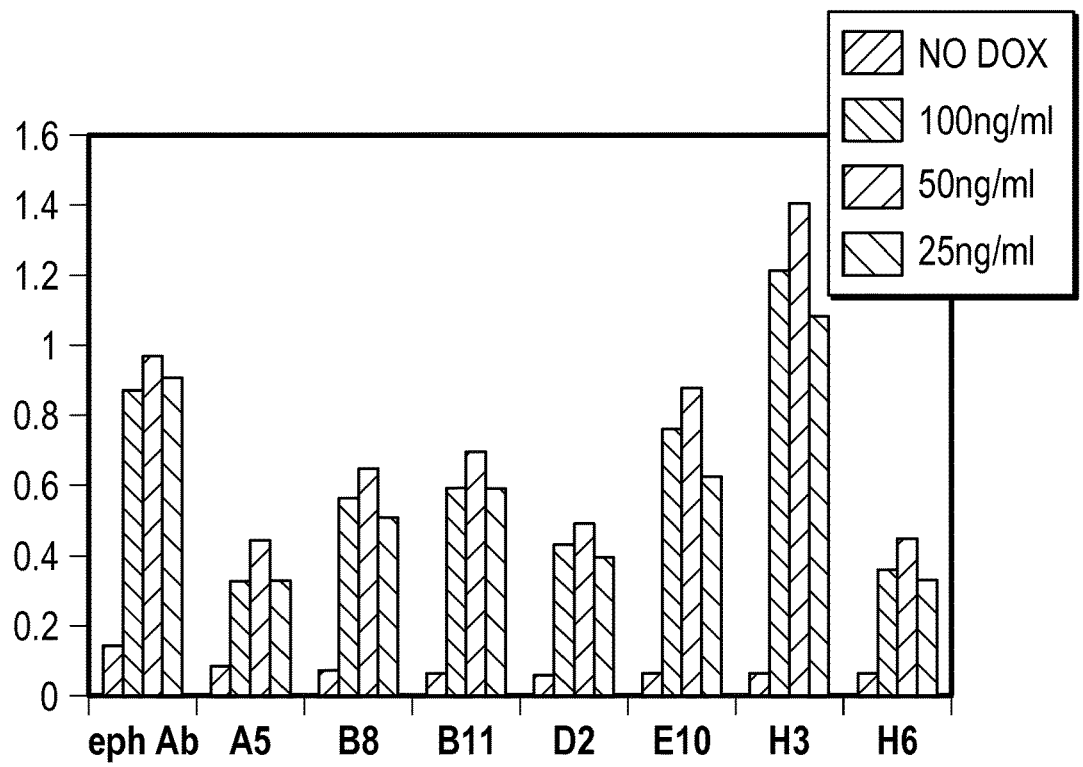
FIG. 4 shows the results of a phage ELISA on HEK293-EphA2 overexpressing cells with individual positives clones A5, B8, B11, D2, E10, H3 and H6.

The variants' ability to recognize the EphA2 receptor in a native conformation was also tested on a stable HEK293 clone overexpressing the EphA2 receptor. As shown in FIG. 4, all the loop 2 variants retain their binding activity to the human EphA2 receptor expressed on the surface of the cell, and clones H3 and E10 preserve their major intensity signal.

B. Protein Production and Testing

Figure 5:
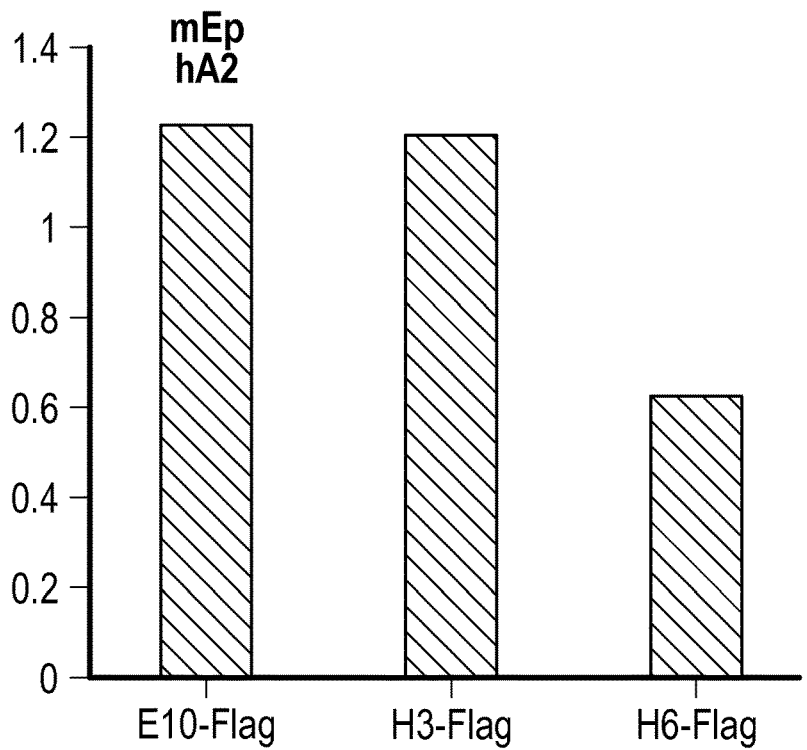
FIG. 5 shows an ELISA on mouse and human EphA2 with the three modified CH2 domains, E10, H3 and H6.
Figure 5:
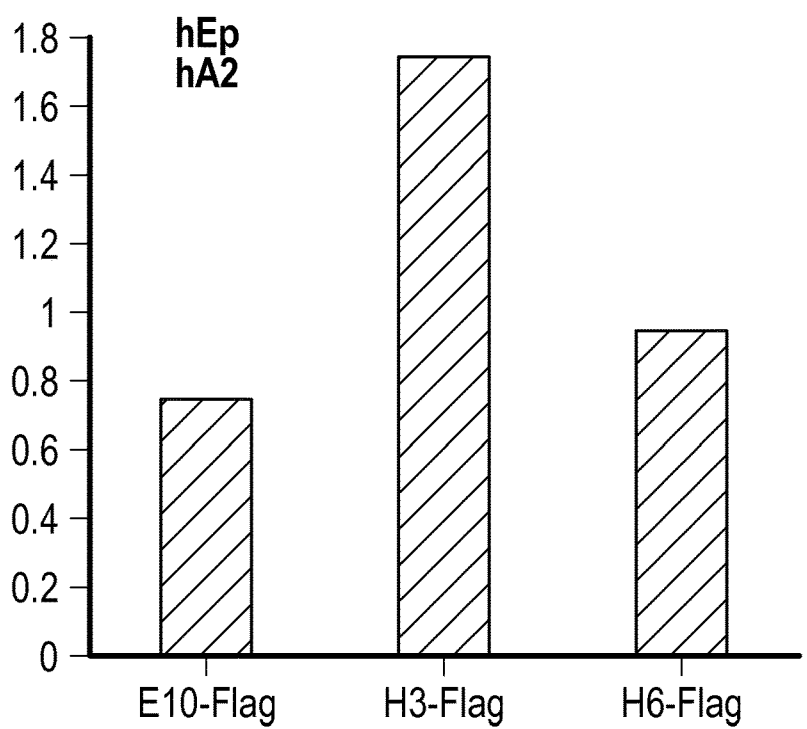

To analyze the behavior of the isolated proteins, the EphA2 binders were subcloned into the periplasmic expression vector pJEX404, expressed into E. Coli HB2151 strain, then extracted from periplasm and purified onto a Nickel column, followed by a gel filtration on a Superdex HR75 16/60 column. The proteins were analyzed in an ELISA assay, coated with either mEphA2 and hEphA2 to confirm the binding capability to the target. All the proteins, except A5 whose expression was unsuccessful, preserved their binding capability, even with different strength where E10, H3 and H6 work better. Binding of the E10, H3 and H6 variants to FcRn and to the target mEphA2 was also analyzed by surface plasmon resonance (SPR) to measure the potency of the binding to the receptor. The binding properties of the three variants is summarized in FIG. 5 where the E10 variant bound to FcRn with about the same $K_D$ ($K_D$=3.26 μM) as the wild type CH2D ($K_D$=1.66 μM), while the $K_D$ for mEphA2 for the three variants ranged from 97 to 873 nM.

TABLE 3

$K_D$ measured with Biacore 3000 on mEphA2

| | mEphA2 | | |
|---|---|---|---|
| Binder | $K_D$ (M) | $K_a$ (1/Ms) | $K_d$ (1/s) |
| E10 | $9.7 \times 10^{-8}$ | $7.91 \times 10^4$ | 0.008 |
| H3 | $3.83 \times 10^{-7}$ | $3.64 \times 10^4$ | 0.014 |
| H6 | $8.73 \times 10^{-7}$ | $9.61 \times 10^3$ | 0.008 |

C. Affinity Maturation of Binders

For the affinity maturation, clones E10 and A9 were chosen as representing the 2 different consensus families and they also showed higher expression and binding in the CIS display format. The affinity maturation libraries were built by introducing diversity in loop 1 as it is neighboring loop 2 (compared to loop 3 which is spatially further away). Two loop lengths were designed, a smaller loop where residues Ser267 to Asp270 (as referenced to FIG. 1) were mutated, or a longer loop comprising Val266 to Pro271 (as referenced to FIG. 1). As before, the libraries were built using trinucleotide oligonucleotides using the same 12 residues as in the primary libraries. The affinity maturation was performed using CIS display on mouse EphA2, using increased washing stringency and decreasing target concentration in an attempt to select for the tightest binders. The output from the selection was cloned into a cytoplasmic expression vector, transformed in Shuffle cells and the expressed proteins screened by ELISA. From the ELISA, 21 mouse EphA2 binding clones were sequenced and found to exclusively carry loop 2 from the parental clone E10, none from H3. Moreover, loop 1 sequences are derived only from the longer loop length library, possibly explaining why library #13 failed to yield any binders in the naïve selection as the length of the loop is important for structural integrity of the modified CH2 domains or functional binding to EphA2.

The nine clones displaying the highest ELISA signal were expressed and purified. The sequence of loop 1 from the four best expressing clones demonstrates two distinct consensus sequences (Table 4): clones D2 and B11 shared the motif Y-x-A-x-x-L (SEQ ID NO: 41) and G7 and B6, P-x-L-x-x-D (SEQ ID NO: 42). The expression level was consistent with the motif: clones G7 and B6 showed a better yield in expression than D2 and B11.

TABLE 4

Sequences in loop 1 of clones selected from affinity maturation.

| Clone | Loop 1 | SEQ ID NO: |
|---|---|---|
| D2 | YEAAAL | 50 |
| B11 | YRADYL | 51 |
| G7 | PHLGVD | 52 |
| B6 | PYLHDD | 53 |

Figure 6A:
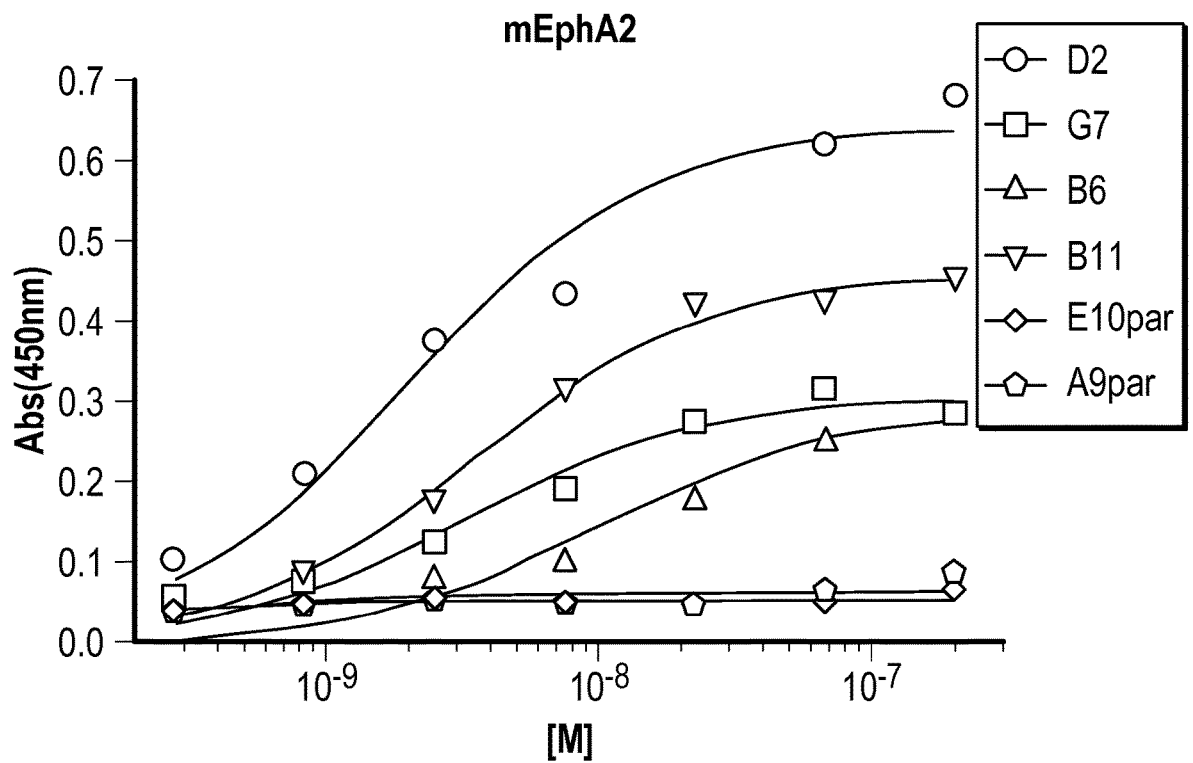
FIG. 6A-B show a titration ELISA on mouse (FIG. 6A) and human (FIG. 6B) EphA2.
Figure 6B:
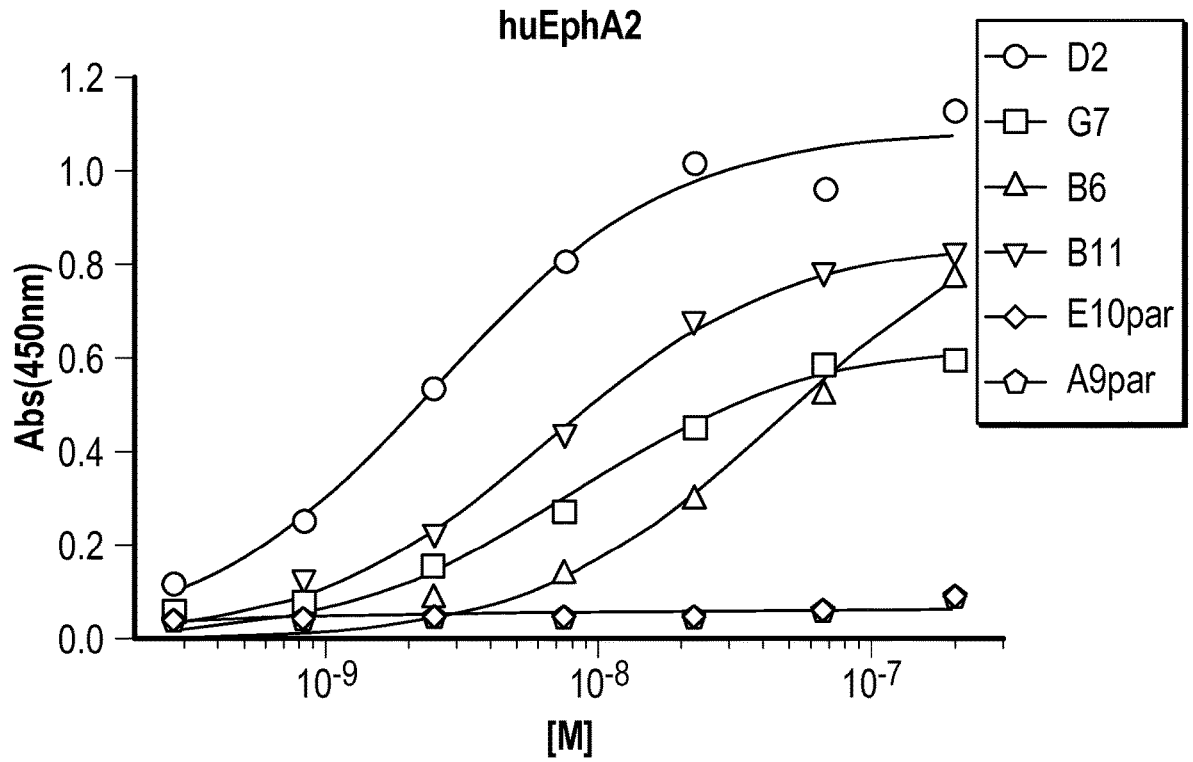
Figure 7A:
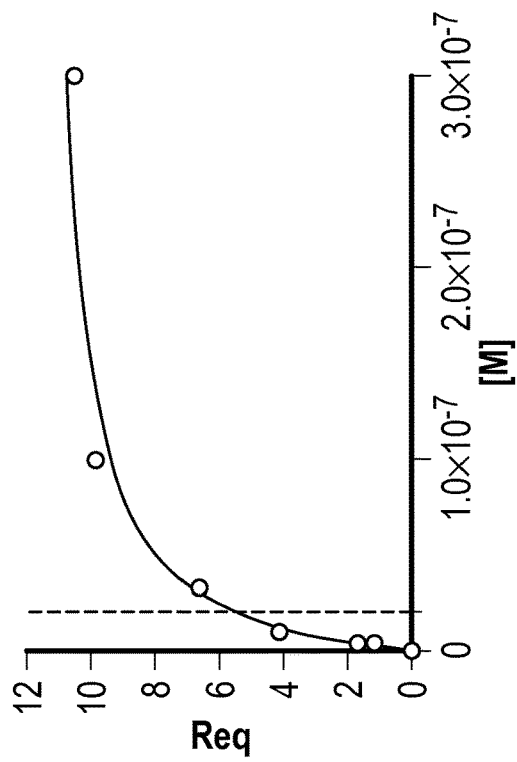
FIG. 7A-C show Surface Plasmon Resonance (SPR) Sensograms of modified CH2 domains binding to human EphrinA2 receptor.
Figure 7A:
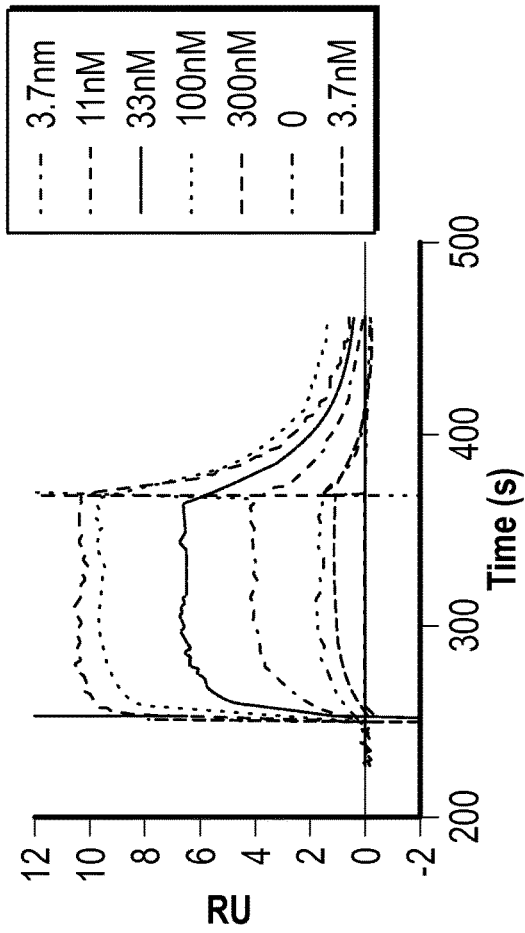
Figure 7B:
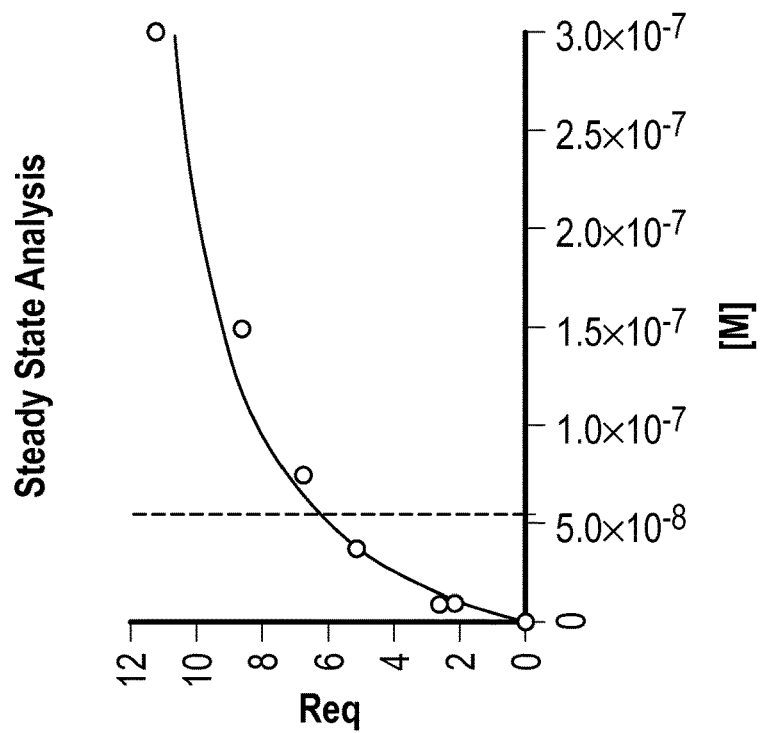
Figure 7B:
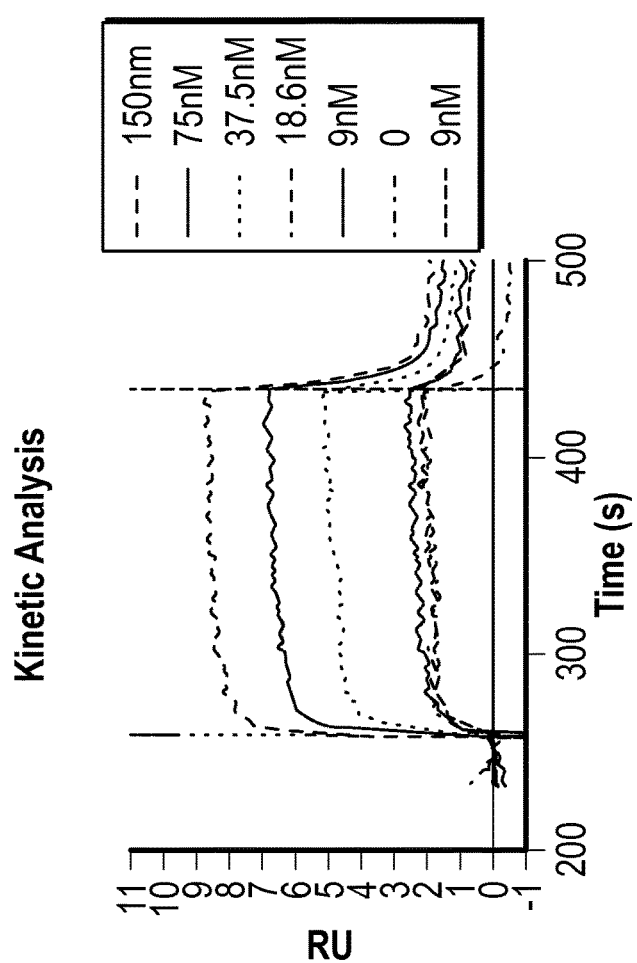
Figure 7C:
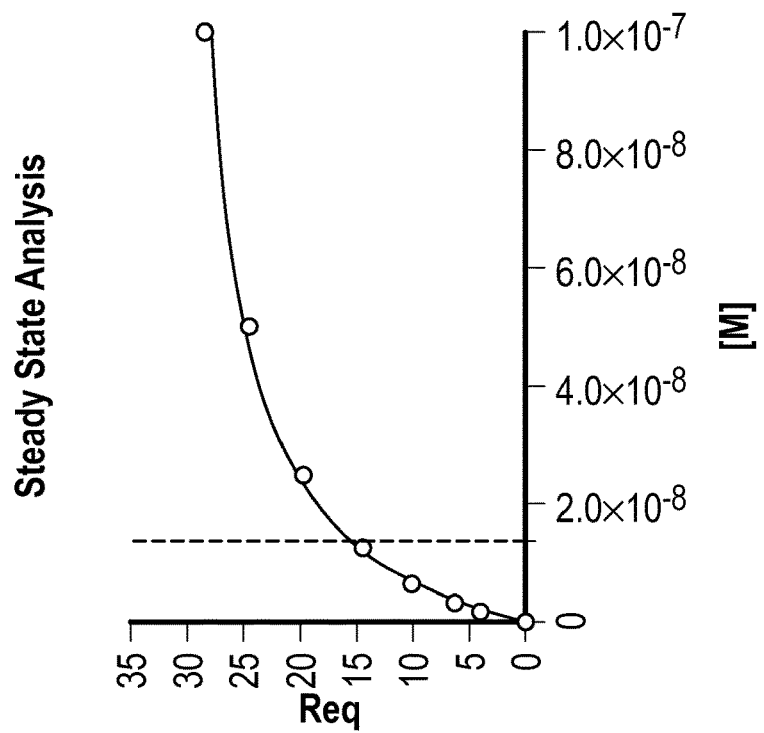
Figure 7C:
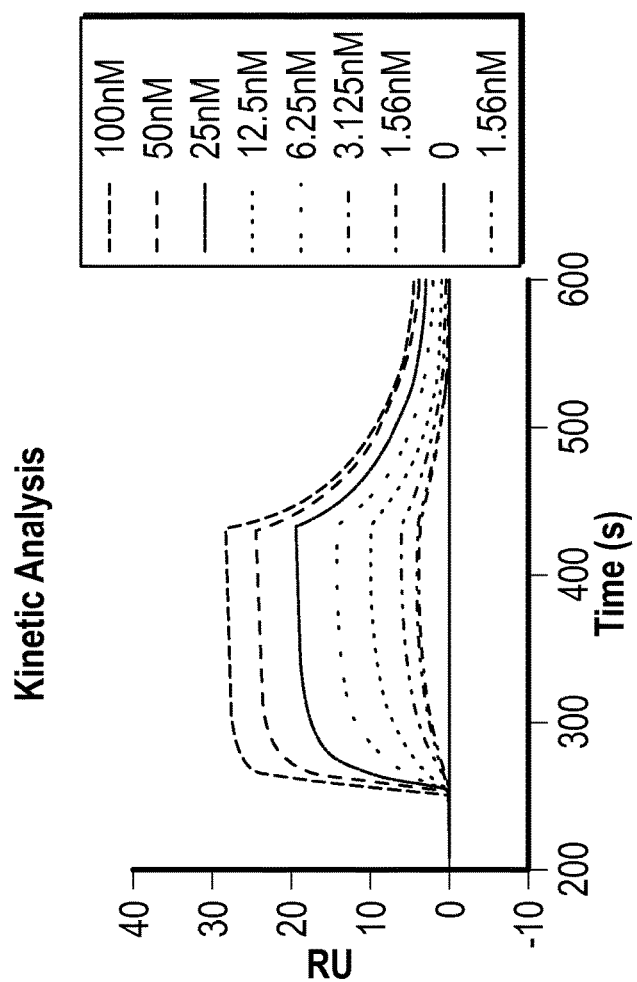

In experiments to determine the affinity of the clones, an end-point titration ELISA of the four anti-EphA2 modified CH2 domains was used to establish an EC50 against human and mouse EphA2. See Table 5 and FIGS. 6A and 6B. Binding of parental clones (E10 and H3) could not be detected at the concentrations tested, yet for the affinity matured clones low nanomolar values were calculated, with little difference between human and mouse orthologs, which is consistent with the fact that both proteins share 95% similarity.

TABLE 5

EC50 of binding to human and mouse EphA2, determined by titration ELISA.

| | mEphA2 | | huEphA2 | |
|---|---|---|---|---|
| Clone | EC50 (M) | $R^2$ | EC50 (M) | $R^2$ |
| D2 | $1.97\ 10^{-9}$ | 0.97 | $2.55\ 10^{-9}$ | 0.99 |
| B11 | $9.89\ 10^{-9}$ | 0.89 | $4.43\ 10^{-9}$ | 0.98 |
| G7 | $3.18\ 10^{-9}$ | 0.94 | $8.06\ 10^{-9}$ | 0.99 |
| B6 | $3.50\ 10^{-9}$ | 0.98 | $6.54\ 10^{-9}$ | 0.99 |
| E10par | nd | | nd | |
| H3par | nd | | nd | | nd: no binding detected.

In the second assay, the affinity was measured using ForteBio's OctetRed. The affinities were generally about 10 times weaker than those measured by ELISA. See Table 6.

TABLE 6

$K_D$ measured with OctedRed on mouse and human EphA2

| | mEphA2 | | huEphA2 | |
|---|---|---|---|---|
| Clone | EC50 (M) | $R^2$ | EC50 (M) | $R^2$ |
| D2 | $1.8\ 10^{-8}$ | 0.99 | $2.0\ 10^{-8}$ | 0.99 |
| B11 | $5.5\ 10^{-9}$ | 0.86 | $3.1\ 10^{-9}$ | 0.90 |
| G7 | $2.1\ 10^{-8}$ | 0.97 | $1.8\ 10^{-8}$ | 0.99 |
| B6 | $3.0\ 10^{-8}$ | 0.98 | $3.9\ 10^{-8}$ | 0.99 |

D. Surface Plasmon Resonance (SPR)

$K_D$ values were also assessed for G7, B6 and B11 clones using Surface Plasmon Resonance (SPR). Using the amine-coupling kit (Biacore) and the Biacore 3000 immobilization wizard, purified human EphA2 extracellular domain is immobilized at 0.5 µM in acetate pH 5.0 to one of the four flow cells of a CM5 sensorchip (GH Healthcare cat BR-1000-14) to a level of approx. 2000 RU (resonance units). Purified CH2 domain mutants are dialyzed against 10 mM Hepes (pH 6.0), 150 mM NaCl (running buffer), diluted in the same buffer to a range of concentrations (10 µM-0.625 µM) and passed over the sensor chip surface at a flow rate of 40 µl/min.

Each cycle consists of a 60 s analyte injection (the association phase), followed by a 180 s dissociation phase. Regeneration is achieved using a 10 s injection of Running Buffer with a 300 s stabilization period. The data are analyzed using the Biacore 3000 Evaluation software.

Baselines are adjusted to zero for all curves and double-referenced by subtracting a sensorgram of buffer injected over the coated surface from the experimental sensograms to give curves representing specific binding Curves are modeled assuming a simple 1:1 interaction to generate the equilibrium and kinetic data. See FIG. 7. $K_D$ values ranged from 22 nM (G7) to 56 nM (B6). See Table 7.

TABLE 7

KDs measured with Biacore 3000 on huEphA2

| | BIACORE 3000 | | | |
|---|---|---|---|---|
| Binder | $KD_{equilibrium}$ (nM) | $KD_{kinetic}$ (nM) | Kon (1/Ms) | Koff (1/s) |
| G7 | 22 | 21 | 1.80E+06 | 0.0375 |
| B6 | 56 | 69 | 7.16E+05 | 0.0496 |
| B11 | 13.9 | 13 | 1.21E+06 | 0.0158 |

E. Binding on Cells Overexpressing EphA2

Figure 8:
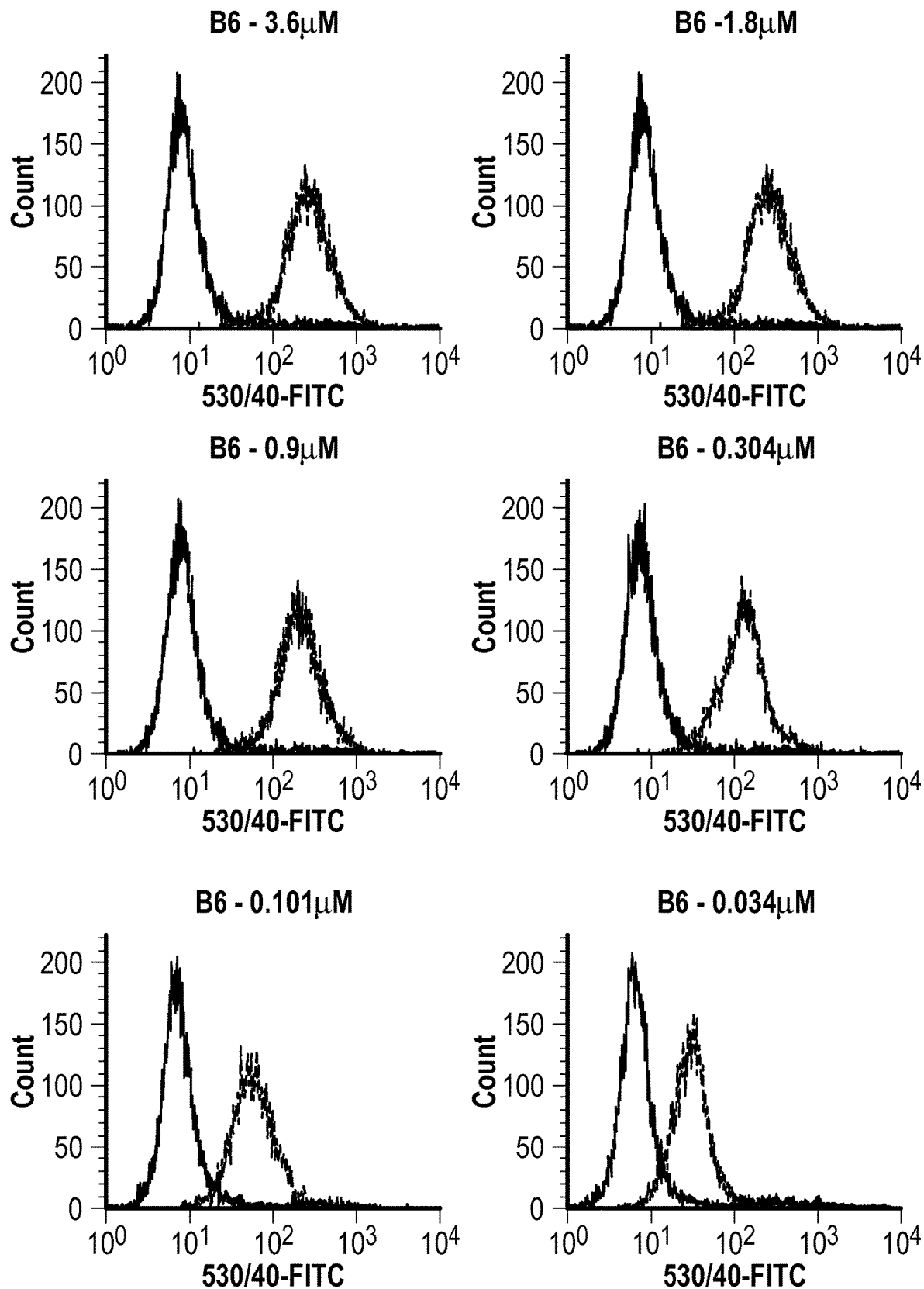
FIG. 8 shows binding of CH2 modified domain B6 in decreasing concentrations to cells transfected with human EphA2 or non-transfected cells.
Figure 8:
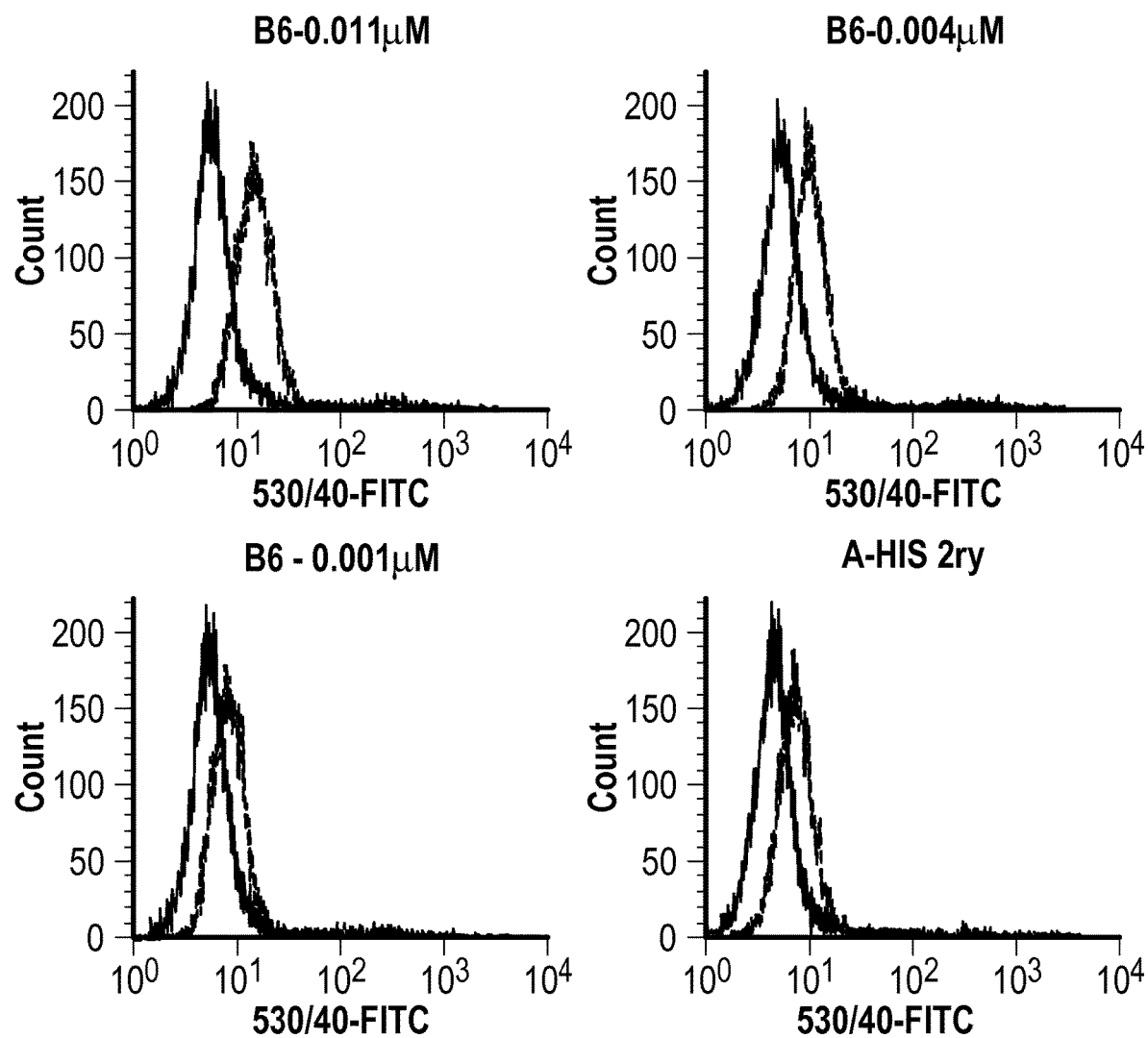
Figure 9:
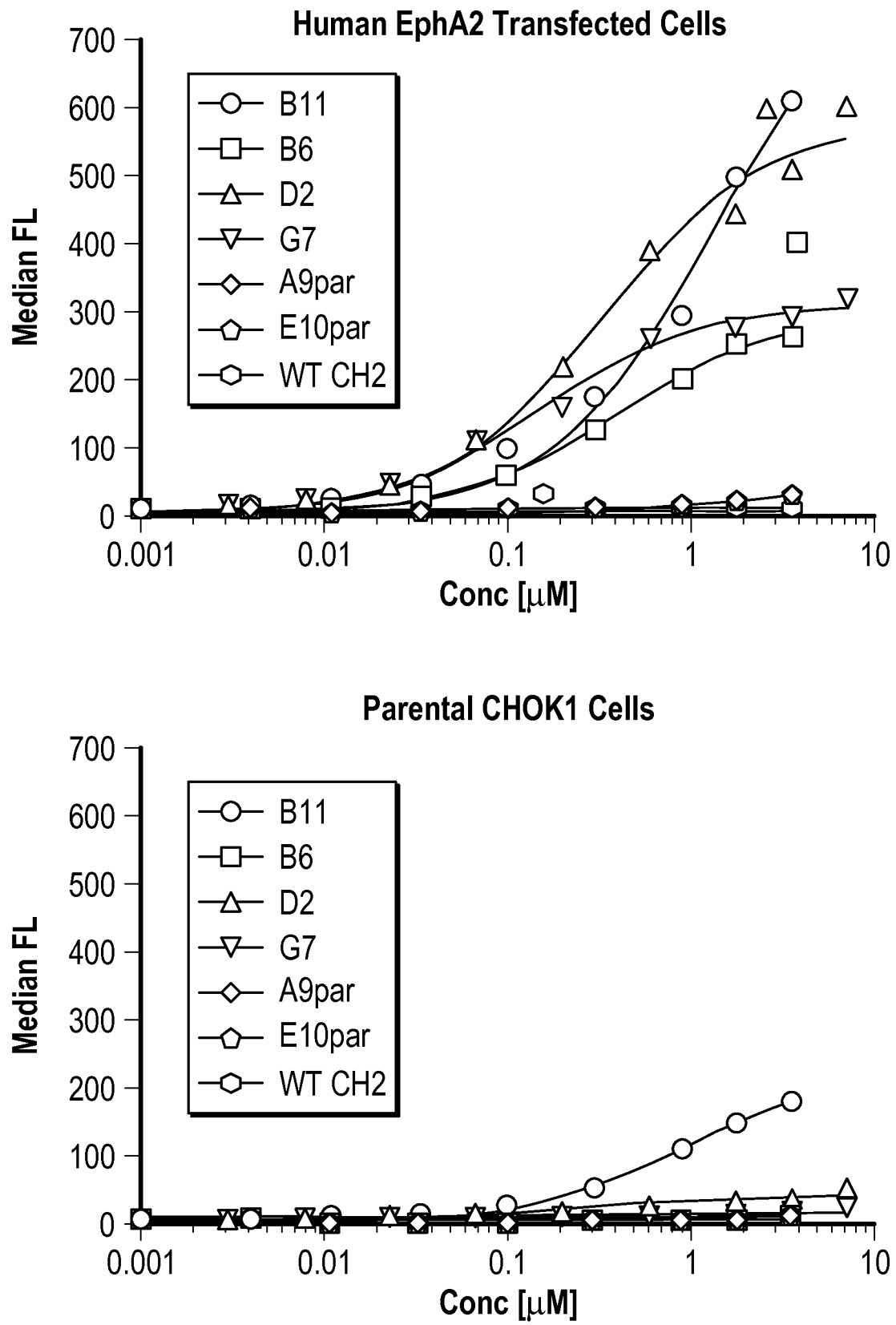
FIG. 9 shows titration of CH2 modified domains (B11, B6, D2, G7 and parental clones A9 and E10 on transfected cells (top) and non-transfected cells (bottom).

CHO cells were transfected with human EphA2 and the binding of the affinity matured CH2 domains was assessed by FACS (FIG. 8). Decreasing concentrations of the CH2 domains were tested and the EC50 values against the target expressed on cells were evaluated (see FIG. 9 and Table 8). Of the four clones, B6 showed the tightest binding to the cells, with little binding to control CHO cells that did not express human EphA2, whereas B11 and to a lesser extent D2 show some signal on non-transfected cells, which might be attributable to cross-reactivity with hamster EphA2 expressed in the immortalized ovarian cells and recognition of a different epitope than B6 and G7 (Chinese hamster EphA2 shares 92% and 94% similarity with human and mouse EphA2, respectively).

TABLE 8

EC50 of binding to EphA2 transfected cells.

| | EC50 (M) | $R^2$ |
|---|---|---|
| D2 | $1.31\ 10^{-6}$ | 0.99 |
| B11 | $4.03\ 10^{-7}$ | 0.99 |
| G7 | $3.33\ 10^{-7}$ | 0.99 |
| B6 | $1.51\ 10^{-7}$ | 0.99 |
| E10par | Nd | |
| A9par | Nd | |
| CH2wt | Nd | |

Nd: no binding detected.

F. Expression and Purification of Proteins

Bioreactor cultivations under controlled conditions were performed using *P. pastoris* as the expression host. In the initial phase, batch-mode with glycerol feed, the culture was grown to wet cell weights of approximately 200 g L-1 without induction of recombinant protein production. The production phase was initiated by supplementation of methanol, inducing the AOX1-promoter. After a total process time of 108 hours with a methanol-induction/recombinant protein production phase of 92 hours, the cells were separated by centrifugation, and the supernatant cleared by filtration to obtain the cell-free filtrate containing the secreted target protein.

Figure 10:
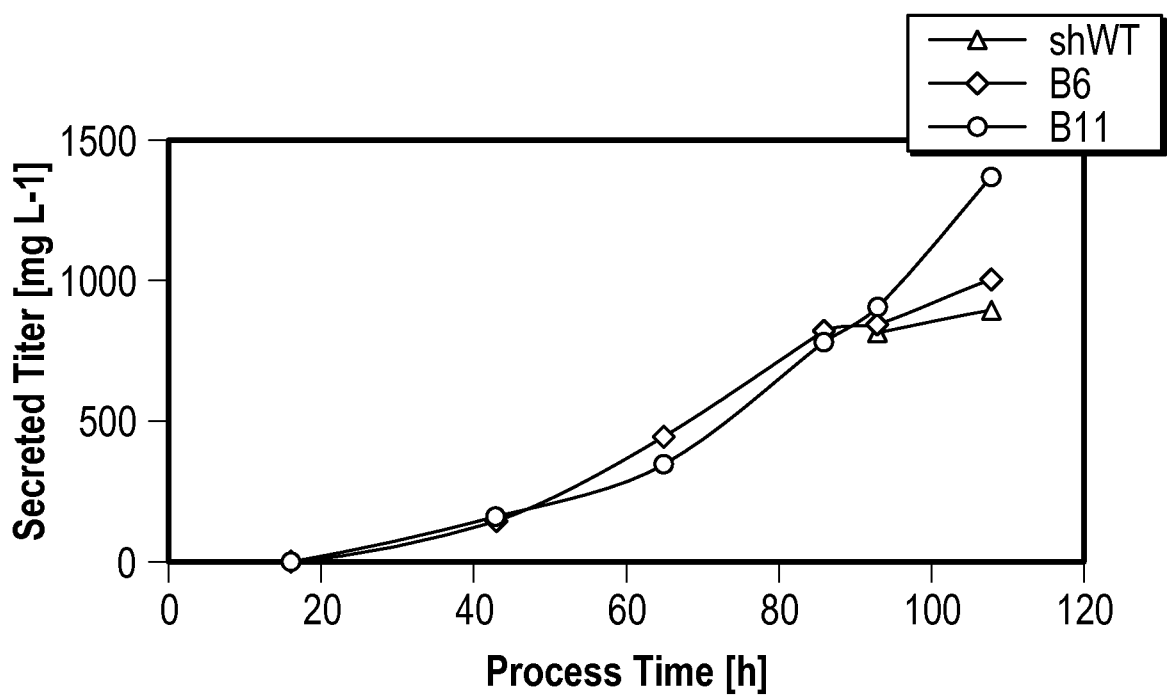
FIG. 10 shows the course of product formation over process time as determined by mCE for B6, B11 and shWT. For shWT, only the last 2 sampling points were analyzed due to the necessity to deglycosylate the protein.
Figure 11:
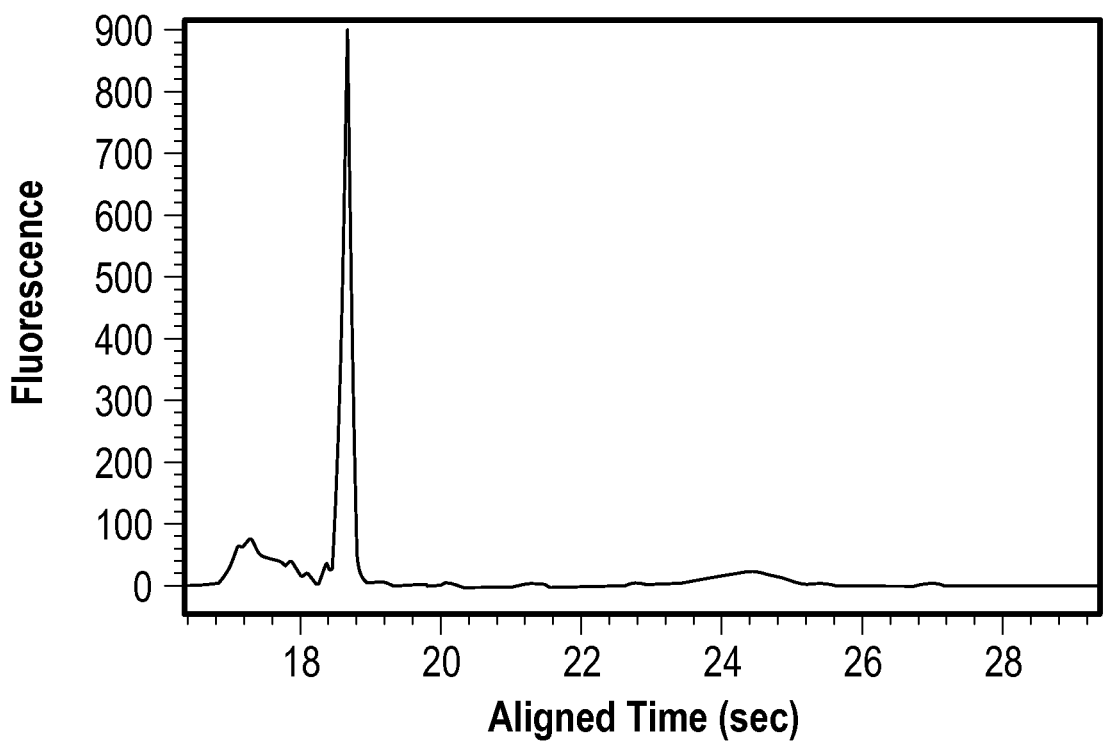
Figure 12C:
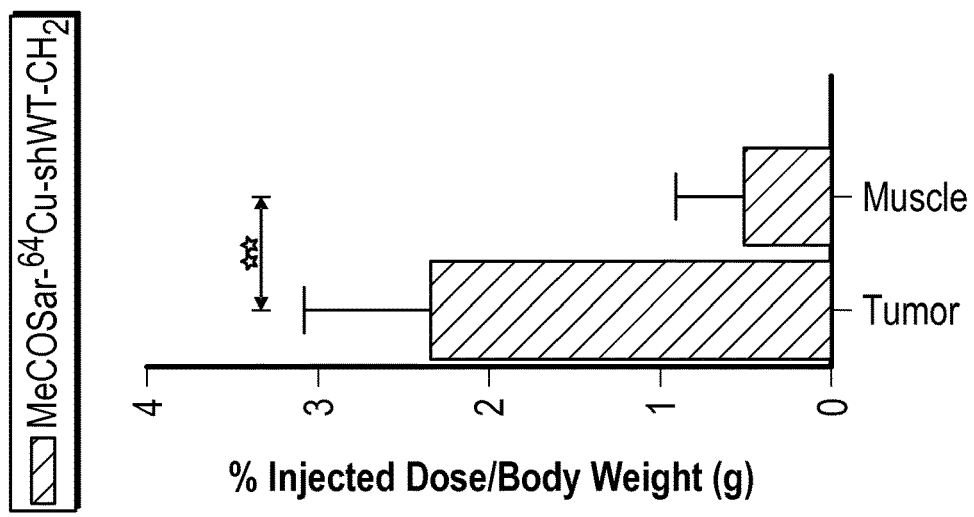
Figure 12B:
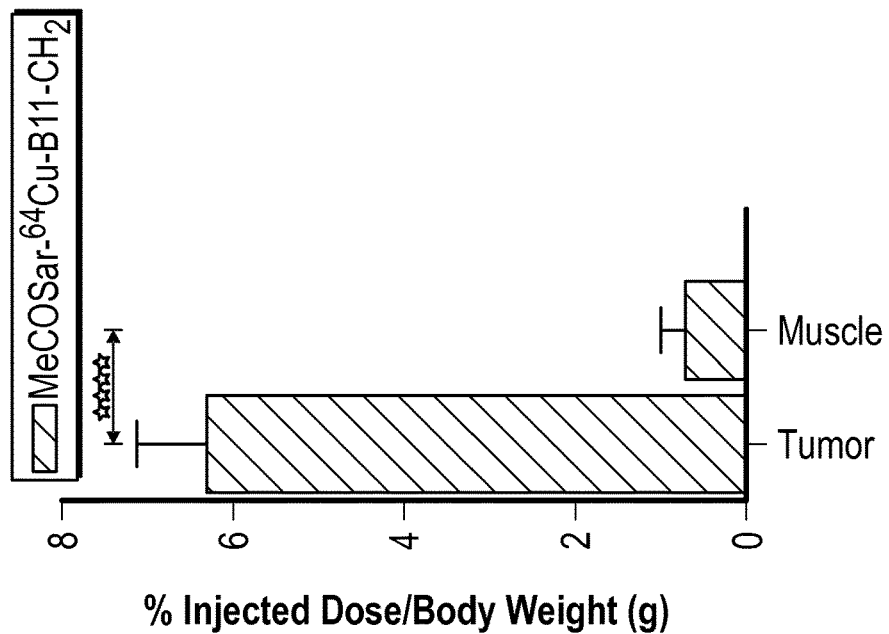
Figure 12A:
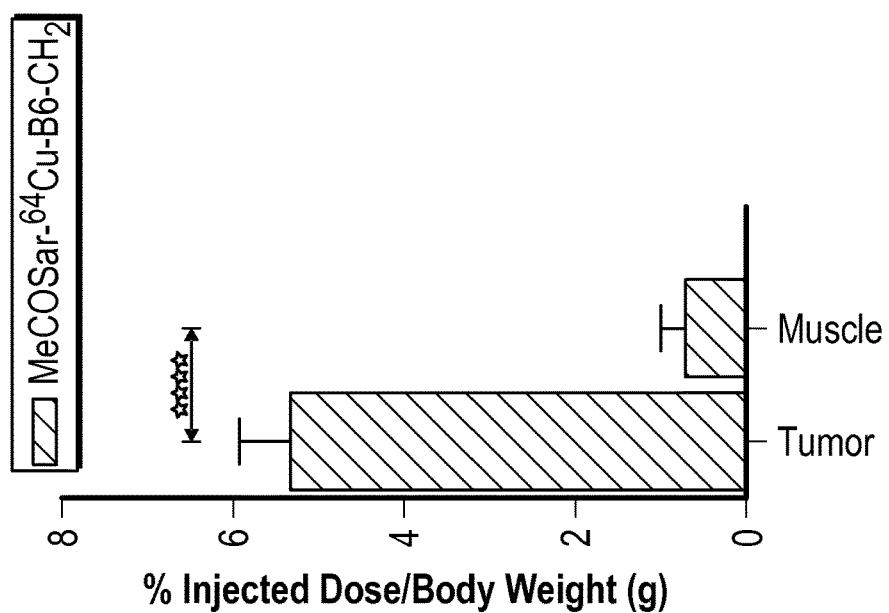
Figures 12D, 12E:
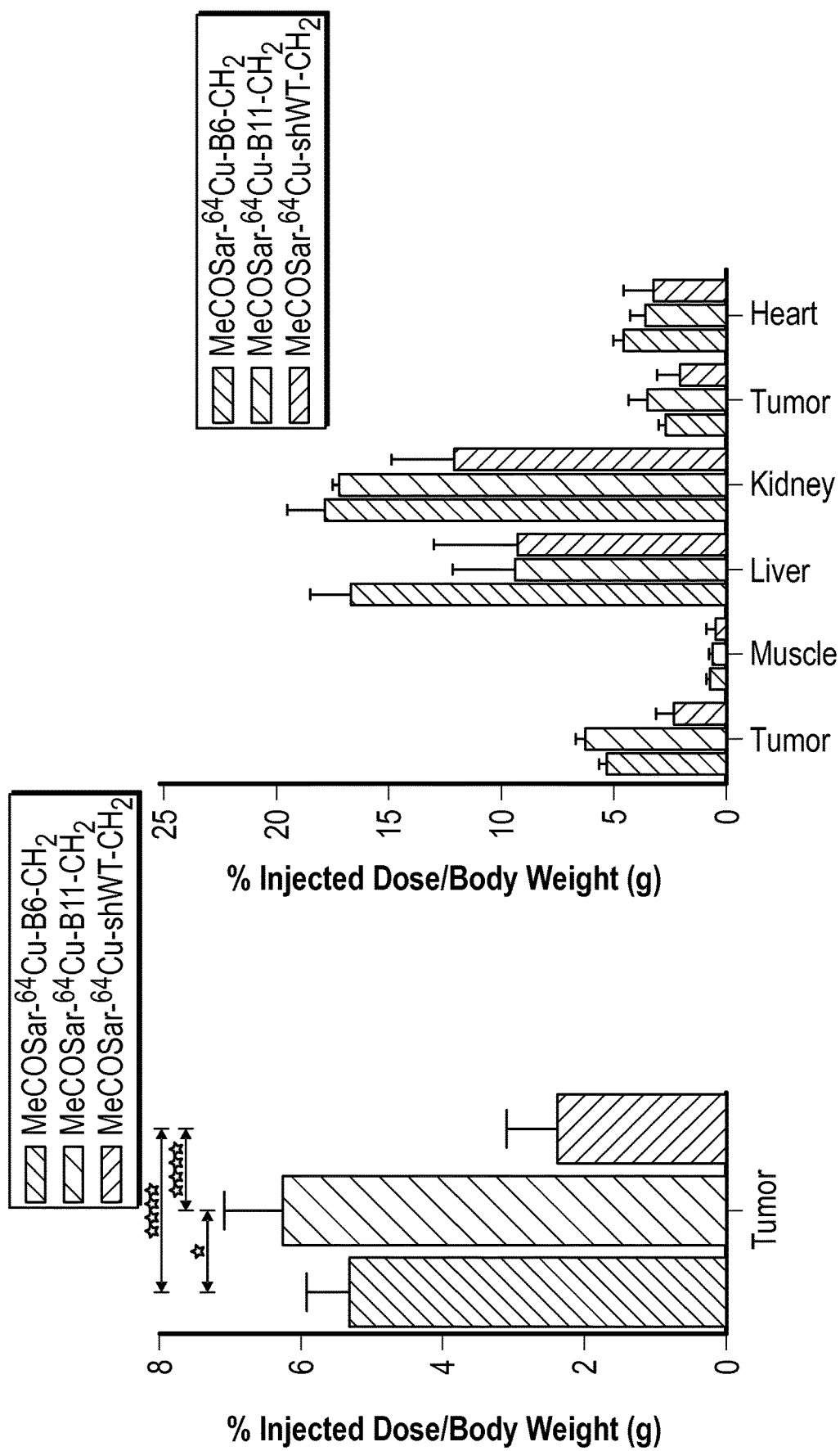

FIG. 10 shows protein production over process time for two modified CH2 domains as measured by microfluidic capillary electrophoresis (mCE). Titers of ~900 mg L-1 (shWT-CH2D, control), ~1,000 mg L-1 (B6) and 1,400 mg L-1 (B11) were obtained after a non-optimized standard 1 L bioreactor cultivation. Purities for all 3 target proteins were above 60% in the final filtrate and the filtrates were affinity-purified by IMAC, polishing was performed using CIEX chromatography, and concentration with ultrafiltration (FIG. 11).

Purified proteins were tested for EphA2 and hFcRn binding using ELISA and Biacore assays and tested on EphA2- expressing cells lines, PC3 and MBA-245 cells. These data confirmed the *Pichia*-produced proteins behaved similar to those produced in *E. coli*.

G. PET/CT Imaging

Targeting and biodistribution characteristics of 2 modified CH2 domains, B6 and B11, engineered to target the EphA2 protein were assessed. B6 and B11 were conjugated to a bifunctional chelator MeCOSar which allowed for labelling the products with the radioisotope copper-64 ($^{64}$Cu) and administered to mice with PC3 prostate cancer xenografts (n=3). MicroPET/CT images were acquired at 3 time points (4, 24 and 48 hours), allowing the identification of the distribution in the whole animal. B6 and B11 showed uptake in the tumors, with B11 providing the highest signal from the PC3 tumors. Uptake was also shown by the B6 product. The negative control shWT_CH2 showed some low level background uptake in the tumor above levels observed in muscle, possibly due to the enhanced permeability and retention (EPR) effect which is known to occur in this xenograft model. Clearance of the CH2 domains was mainly indicated to occur via the liver and the kidneys.

Following the final imaging time point at 48 hours, mice were sacrificed and perfused, and a biodistribution study was performed. Several organs including tumor and muscle were removed and the level of radioactivity measured by a gamma-counter. Results are expressed as % injected dose per g (% ID/g) of tissue at 48 hours. The B11 product showed highest tumor uptake of approximately 6% ID/g compared to muscle of <1%. The B6 product showed tumor uptake of approximately 5% ID/g compared to muscle of <1%. The negative control shWT product contained slightly more than 2% in the tumor above levels observed in muscle of <1%. B6 had much higher liver retention at approximately 17% ID/g than both the B11 (9% ID/g) and the shWT_CH2 control (9% ID/g). Kidney retention was similar between B6 and B11 (approx. 17 to 18% ID/g) and also higher than the control at 12% ID/g. Lung and heart showed little difference between products with <5% ID/g for all products in both organs. See FIG. 12.

Figure 13:
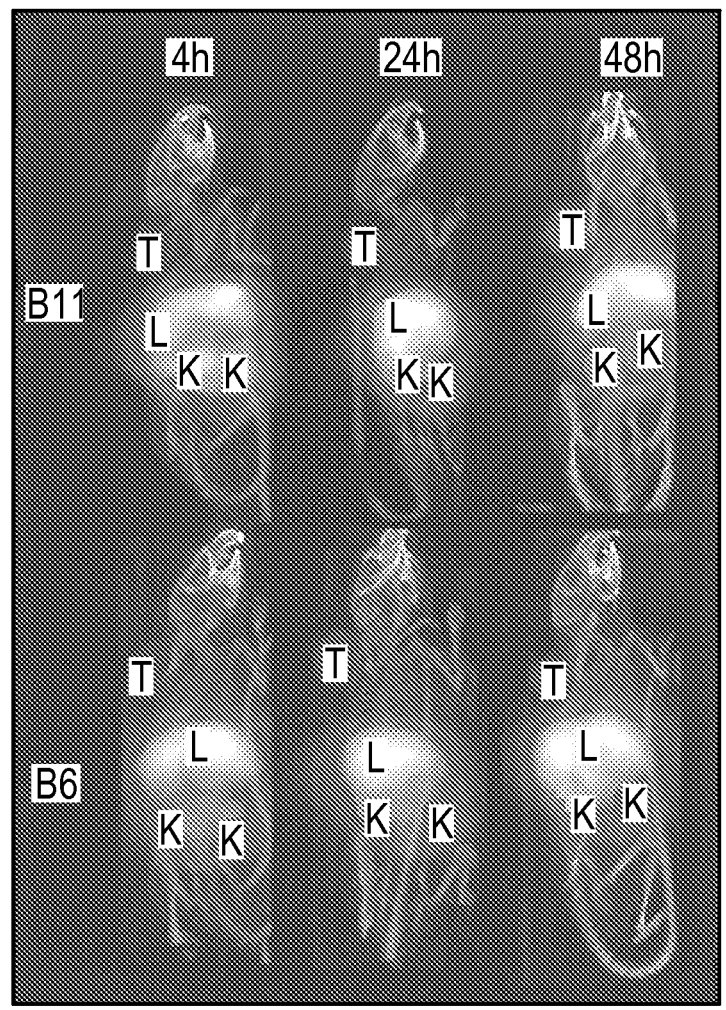
Figure 14:
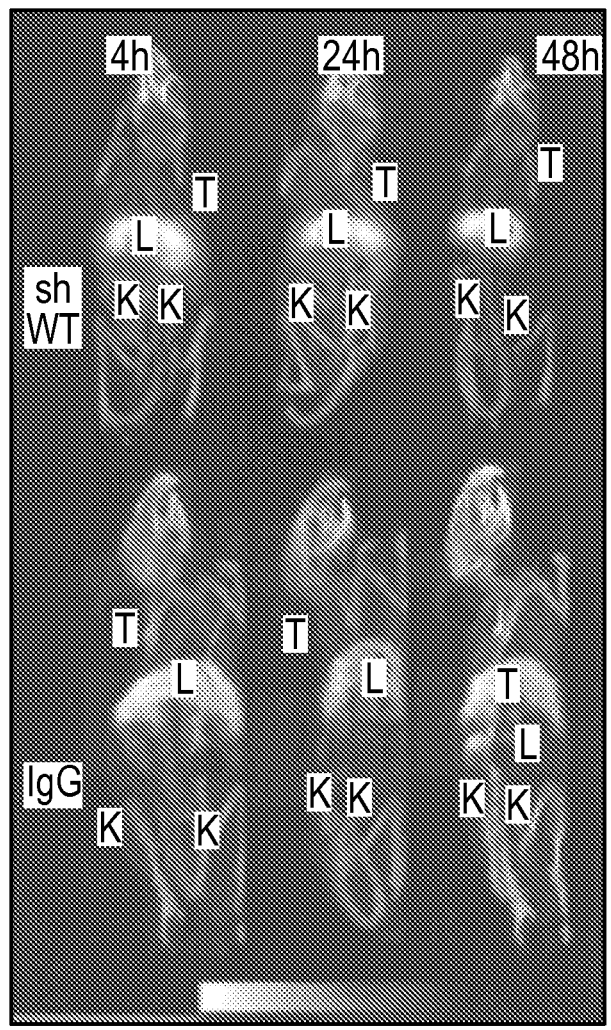

Small-animal PET imaging and Standard Uptake Value (SUV) analysis (see calculation below) of tumor bearing mice revealed an increasing tumor-uptake from 4.11±0.77 at 4 hours, 9.22±0.70 at 24 hours, to 10.89±0.63 at 48 hours after tracer injection for $^{64}$CuMeCOSar-B11, and an accumulation of 3.95±0.99 at 4 hours, 5.17±1.33 at 24 hours, and 4.42±0.89 at 48 hours after tracer injection for $^{64}$CuMeCOSar-B6 (FIG. 13). In contrast, tumor-bearing mice injected with the negative control $^{64}$CuMeCOSar-shWTCH2 showed only minor tracer uptake in their tumors, similar to background activity, at any measured time point and a similar lack of tumor uptake was seen for the positive control IgG, $^{64}$CuMeCOSar-IgG, which binds to EphA2 (FIG. 14). The $^{64}$CuMeCOSar-B11 modified CH2 domain accumulated in the tumor faster and with a stronger SUV compared to the $^{64}$CuMeCOSar-B6 modified CH2 domain.

H. Localization Experiments Via Immunofluorescence Analysis

Figure 15:
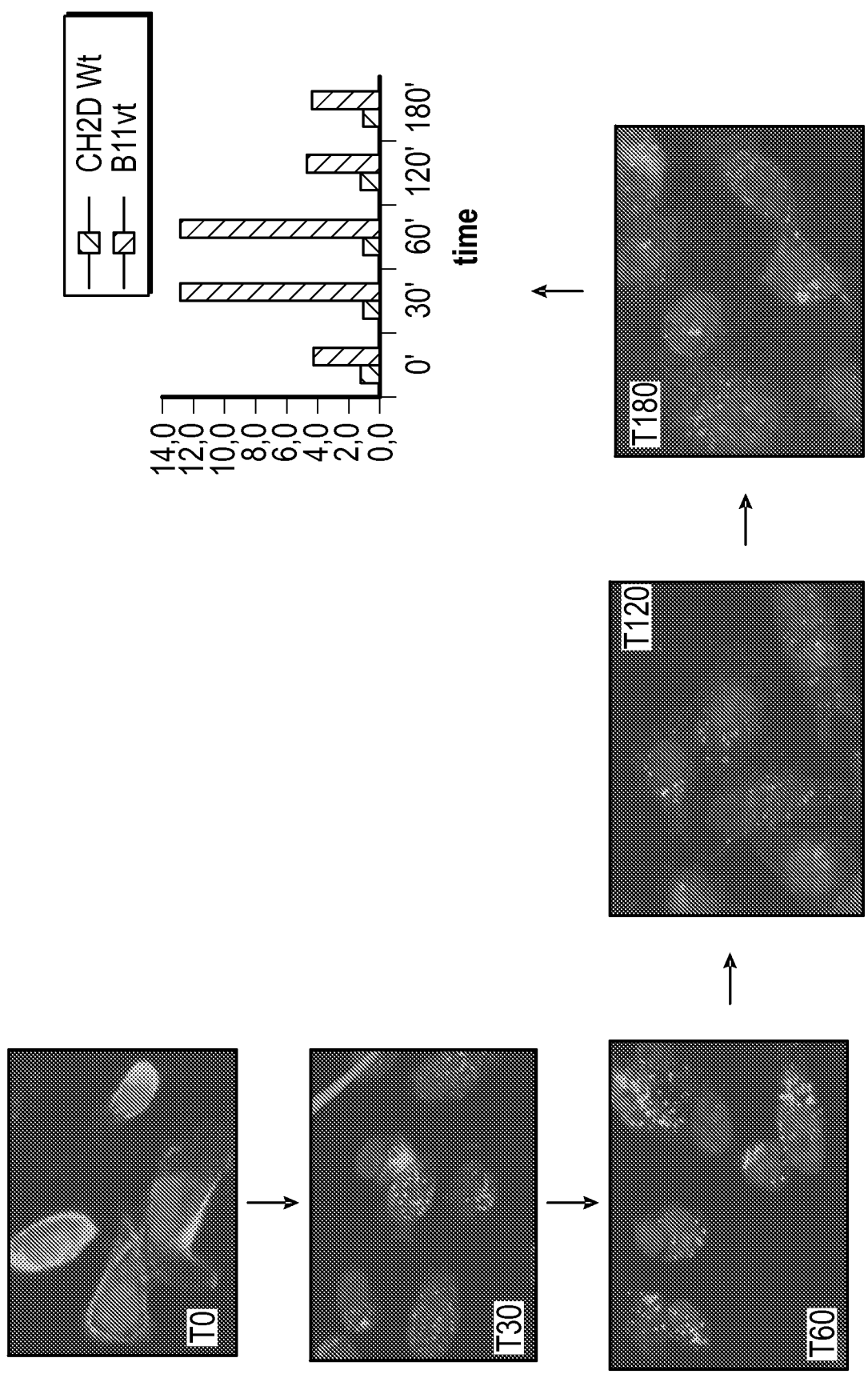
Figure 16:
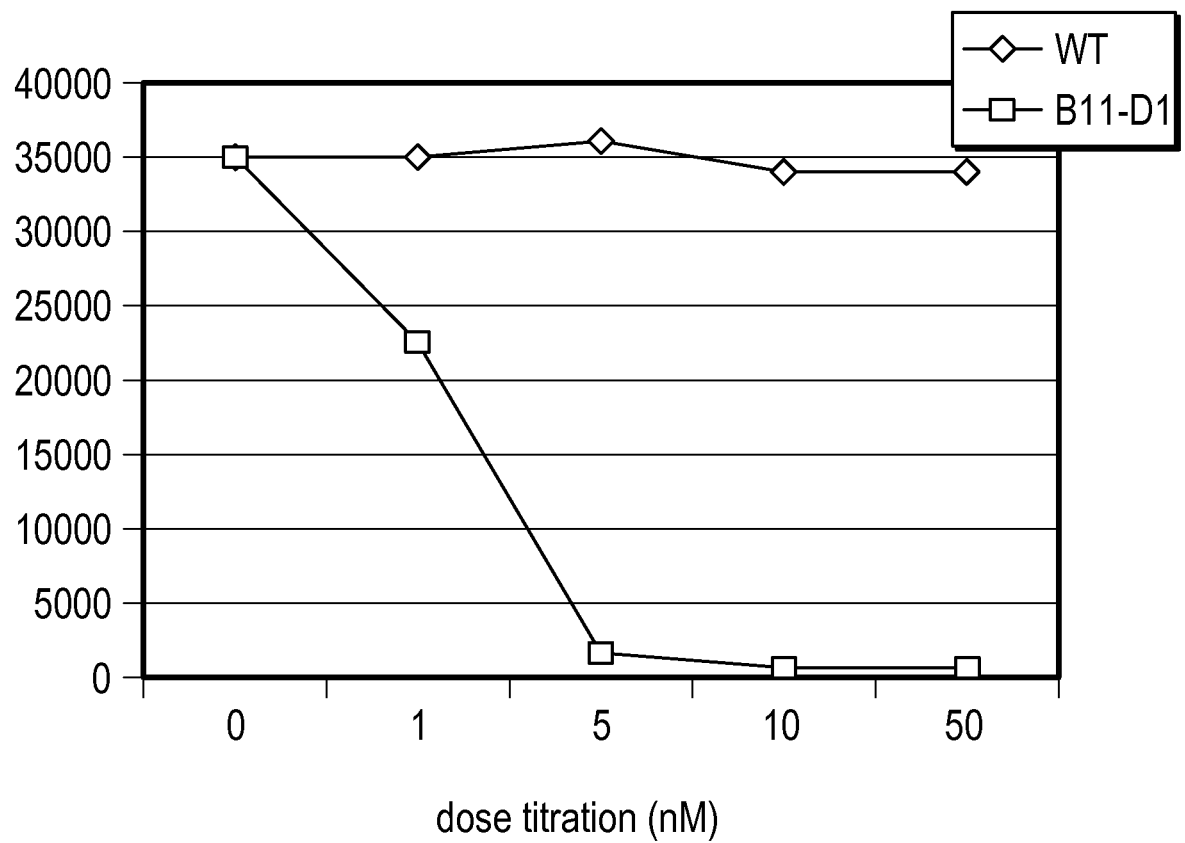

PC3 cells were incubated at 37° C. with B11 conjugated to deimmunized α-sarcin (B11-sarcin) and endosomal or lysosomal vesicles were counted over time. B11-sarcin rapidly internalized and was localized into the early endosomes and endosomes up to 60 minutes. After 60 minutes, the B11-sarcin appeared to localize either into lysosomes and is degraded or is found in the cytoplasm. See FIG. 15. PC3 cells incubated with B11 conjugated to deimmunized α-sarcin at 37° C. for 72 hours at various concentrations demonstrated cell killing with an IC50 of approximately 2 nM. See FIG. 16.

Figure 17:
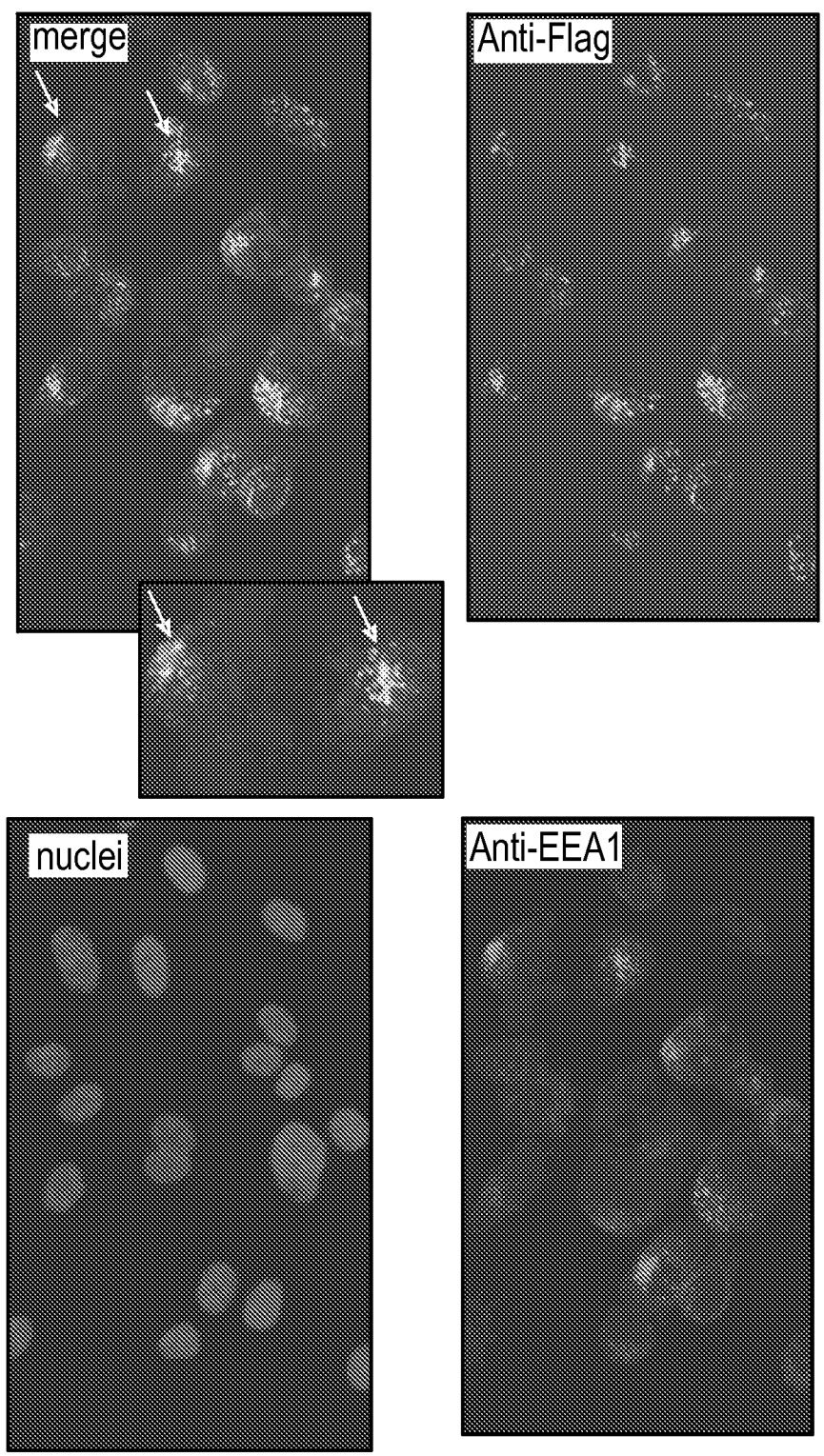

The B11 variant was detected with α-Flag antibody and early endosomes were detected with the anti-EEA1 antibody. In the merged view it appears that B11 is localized in the early endosome. See FIG. 17.

I. Conjugation of Biotin-dPEG11-MAL

Three B11 modified CH2 domains, SEQ ID NO: 89 containing a C terminal cysteine and N terminal hinge sequence, SEQ ID NO: 90 containing an N terminal hinge sequence and SEQ ID NO: 91 containing a C terminal cysteine, were conjugated with discrete polyethylene glycol (dPEG) and biotin to assess binding and internalization in PC3 cells. Conjugation of biotin-dPEG was achieved by incubating the modified CH2 domains for 1 hour at room temperature in 1 mM DTT/10 mM EDTA followed by dialysis against 10 mM HEPES pH7.0, 150 mM NaCl, 2 mM EDTA, 4° C. The modified CH2 domains were then incubated at room temperature overnight with two equivalents of Biotin-dPEG11-(QUANTA BIODESIGN 10195) dissolved in DMSO (10 mg/ml). Unconjugated Biotin-dPEG11 was removed by dialysis against PBSK overnight at 4° C. The reaction was monitored by UPLC on an Acquity BEH300 C4 1.7 μm, 2.1×100 mm (WATERS 186004496) column and characterized by MALDI-TOF (Applied Biosystem VOYAGER-DE STR) using Sinapic acid (Fluka product No 85429) as a matrix.

Figure 18:
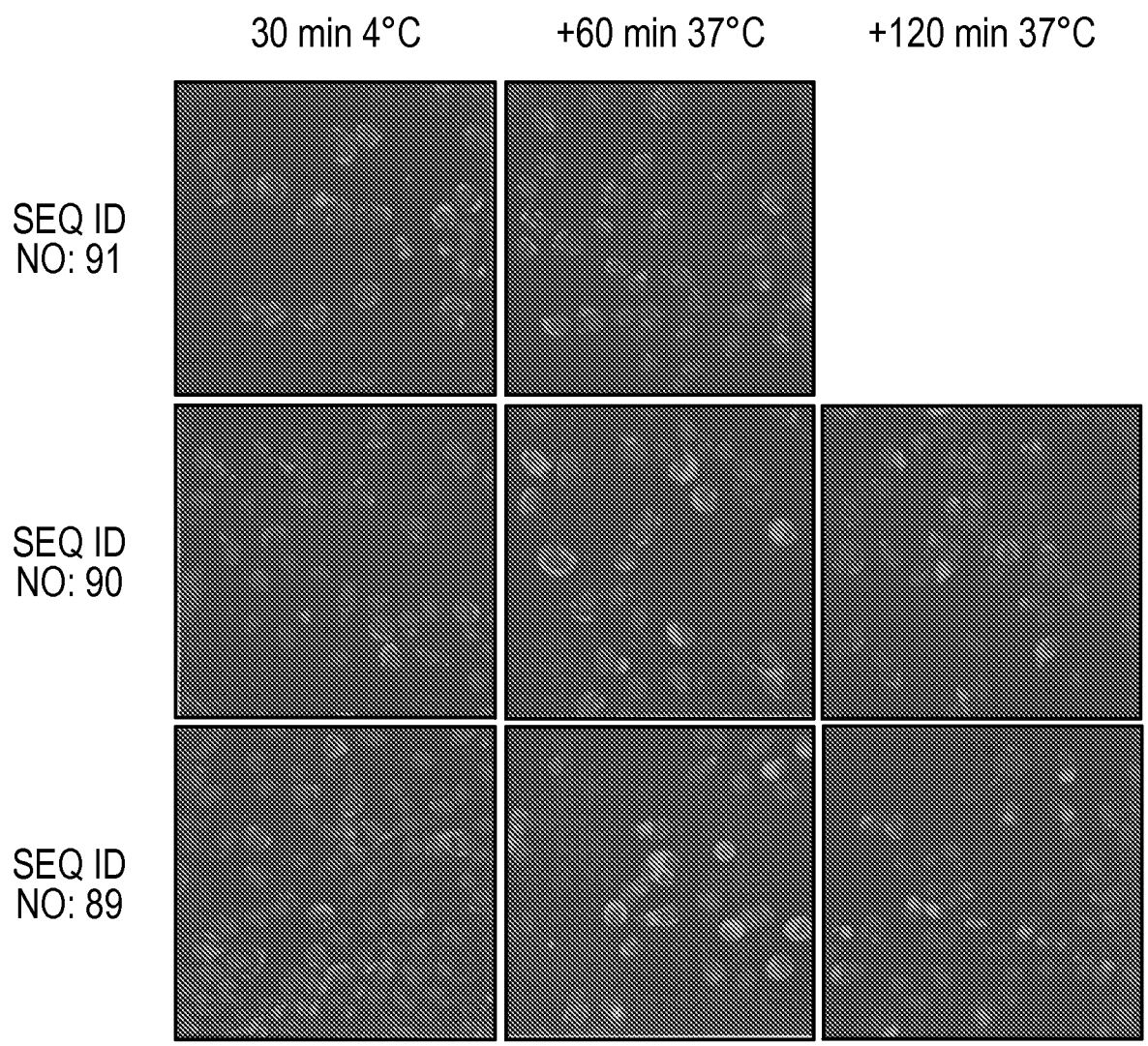

Binding and internalization of the modified B11 CH2 domains to PC-3 cells expressing endogenous EphA2 receptor were evaluated by immunofluorescence. PC-3 cells were incubated with the various proteins at 4° C. for 30 minutes to allow binding to the EphA2 receptor on the cell surface and to block internalization (FIG. 18, left column) After binding at 4° C., plates were moved to 37° C. to allow internalization, and the cells imaged after 60 minutes and 120 minutes. As shown in FIG. 18, all three of the modified B11 CH2 domains bound (left column) and internalized (middle and right columns) to PC-3 cells.

Example 2. Materials and Methods

The results obtained in Example 1 were obtained using the following materials and methods.

A. Chemicals and Materials

Synthetic genes were purchased from DNA2.0 (Menlo Park, Calif., USA). For plasmid isolation, the PureYield™ Plasmid Miniprep System of Promega (Madison, Wis., USA) was used. All DNA-modifying enzymes were obtained from Fermentas GmbH (Burlington, Ontario, Canada). If not stated otherwise, chemicals were purchased from Becton, Dickinson and Company (Franklin Lakes, N.J., USA), Fresenius Kabi Austria (Graz, Austria) and Carl Roth (Karlsruhe, Germany).

B. Media

For *E. coli* standard LB-medium containing 25 μg/ml Zeocin was used. YPhyD for *P. pastoris* contained 10 g/l yeast extract, 20 g/l phytone peptone and 20 g/l glucose. For antibiotic selection in *Pichia* 100 μg/ml Zeocin (Eubio, Austria) was used. 15 g/l agar was added for plate media. Buffered minimal media BMD (1%), BMM2 and BMM10 contained per liter: 200 ml 1 M sodium phosphate buffer (pH 6), 13.4 g yeast nitrogen base without amino acids, 0.0004 g/l biotin and 11 g/l glucose or 1 or 5% (v/v) methanol, respectively. All pre-cultures were prepared using YPhyD medium containing 20 g/l phytone peptone, 10 g/l Bacto-Yeast Extract and 20 g/l glucose. BSM medium contained per liter CaSO$_4$:2H$_2$O 0.47 g, K$_2$SO$_4$ 9.1 g, KOH 2.07 g, MgSO$_4$:7H$_2$O 7.5 g, EDTA 0.6 g, H$_3$PO$_4$ (85%) 13.4 ml, Glycerol 40.0 g, NaCl 0.22 g and 4.35 ml PTM1. PTM1 Trace elements solution contained per liter 0.2 g Biotin, 6.0 g CuSO$_4$.5H$_2$O, 0.09 g KI, 3.0 g MnSO$_4$.H$_2$O, 0.2 g Na$_2$MoO$_4$.2H$_2$O, 0.02 g H$_3$BO$_3$, 0.5 g CoCl$_2$, 42.2 g ZnSO4.7H$_2$O, 65 g Fe(II)SO$_4$.7H$_2$O and 5 ml H$_2$SO$_4$. The fed-batch media were either 60% (w/w) Glycerol or concentrated Methanol and were supplemented with 12 ml/l PTM1 mineral salts solution.

C. Construction of Expression Plasmids and Resulting P. pastoris Strains

Synthetic genes were cloned into the multiple cloning site of the Zeocin-resistance E. coli/P. pastoris shuttle vector pPpT4 via XhoI/NotI sites, downstream of the wildtype AOX1 promoter. See Nääksaari, et al. "Deletion of the Pichia Pastoris Ku70 Homologue Facilitates Platform Strain Generation for Gene Expression and Synthetic Biology."0.2012, PLoS ONE 7, 7:e39720, herein incorporated by reference in its entirety.

Plasmids were linearized with either BglII, ethanol-precipitated and desalted. Electro-competent P. pastoris CBS 7435 mutS cells (Näätsaari et al. 2012) were prepared and transformed with 2 μg of the BglII-linearized pPpT4 vector constructs according to Lin-Cereghino et al., "Condensed protocol for competent cell preparation and transformation of the methylotrophic yeast Pichia pastoris," 2005, Biotechniques, 38:44, 46, 48, herein incorporated by reference in its entirety. Transformants were plated on YPD-Zeocin (100 μg/ml Zeocin) agar plates and grown at 28° C. for 48 hours.

D. Micro-Scale Cultivation

P. pastoris strains expressing the target genes were cultivated in 96-deep well plates as described by Weiss H. M. et al. "Expression of functional mouse 5-HT$_{5A}$ serotonin receptor in the methylotrophic yeast Pichia pastoris: pharmacological characterization and localization," FEBS Lett. 1995, 377:451-456, herein incorporated by reference in its entirety.

E. Fed-Batch Bench-Scale Bioreactor Cultivations

Pre-cultures of individual strains were grown in 50 and 200 ml YPhyD medium containing 20 g/l Bacto-Yeast Extract and 20 g/l glucose in wide-necked, baffled shake flasks at 120 rpm at 28° C. Each bioreactor (Infors Multifors system (Infors AG, Bottmingen, Switzerland)) containing 450 ml BSM-media (pH 5.0) was inoculated from the pre-culture to an OD600 of 2.0. During the batch phase P. pastoris was grown on glycerol (4%) at 28° C. At the beginning of the glycerol feeding phase the temperature was decreased to 24° C. For methanol-fed cultures, the fed-batch phase was started upon depletion of initial batch glycerol with 16 g/(1*h) glycerol feed solution followed by methanol induction. In the early stages, the methanol-feed was set to 2 g/(l*h) and was gradually increased within the next 70 h to 6 g/(l*h). Likewise, the glycerol-feed was phased down during the first hour of methanol induction to 0 g/(l*h). Dissolved oxygen was set to 30% throughout the whole process. After 92 h of methanol induction the bioreactor cultivations were stopped.

F. Target Protein Analysis and Quantification

Microfluidic capillary electrophoresis using the LabChip® GX II (Caliper LS, PerkinElmer, USA) was used to detect and quantify the target proteins. Briefly, several μL of all culture supernatants or bioreactor samples (taken at different time-points throughout the process) are fluorescently labeled and analyzed according to protein size, using an electrophoretic system based on microfluidics. Internal standards enable approximate allocations to size in kDa and approximate concentrations of detected signals. External standards (as e.g. authentic standard material, which was not available; instead, cytochrome c as external standard protein with a similar molecular weight) guarantee more precise allocation of protein signals. Standard deviations of this robust system are usually below 10%, even at high protein loads. More specifically, proteins were quantified by calibrating the integrated areas of the protein-specific peaks in the electropherograms to an external reference protein standard (Cytochrome c) of known concentration. For glycosylated proteins, peak areas of diluted deglycosylated samples were compared to those of untreated samples to compensate for glycosylation-related differences in quantification. Samples were treated with EndoH for deglycosylation according to the manufactures instructions (NEB, USA, catalog# P0702L). The dilutions of samples were in a range to give peak areas of the samples that were comparable to those of the reference protein standard.

G. Target Protein Purification

Chromatography was performed using an ÄKTA Avant 150 system with a HisPrep 16/10 FF Ni-NTA column (both GE Healthcare). Buffers used were 20 mM NaPi, 500 mM NaCl, pH 7.4 (buffer A) and 500 mM Imidazol, 20 mM NaPi, 500 mM NaCl, pH 7.4 (buffer B). For the runs, pH and conductivity of the samples were adjusted to the values of the loading buffer using NaOH and NaCl. Samples were filtered through a 0.2 μm filter prior to loading. The following protocol was established and applied for all three products: after equilibration at 0% B for 2 column volumes (CV), 200 mg of each sample protein was loaded, followed by a wash step of 0.5 CV at 0% B, a wash step of 3 CV at 8% B (40 mM Imidazole) and an elution step of 3 CV at 60% B (300 mM Imidazole). Samples were collected in 10 mL fractions. The column was washed at 100% B (500 mM Imidazole) for 2 CV and re-equilibrated for the next run at 0% B for 5 CV.

Cation exchange (CIEX) chromatography was selected as polishing step and to exchange buffer to PBS, pH 7.4 (used as elution buffer in CIEX. Samples (pooled IMAC fractions) were diluted to conductivity <8 mS/cm using MilliQ water and applied to a HiPrep 16/10 SP Sepharose FF column (GE Healthcare). Buffer A used for column equilibration and washing was 20 mM Sodium Phosphate, pH 7.4. Buffer B used for step elution was PBS, pH 7.4 (Gibco). Eluate was collected in 14 mL fractions and pooled after analysis.

After purification via Ni-NTA- and CIEX-chromatography as well as concentration using ultrafiltration (5 kDa cut-off; Vivaspin20 devices, Sartorius), final samples were analyzed by mCE in comparison to cytochrome c. The concentration was determined by spectrophotometrical analysis at 280 nm, and the Endotoxin-content was measured by LAL-assay.

H. Library Synthesis

Trimer primers were synthesized by Ella Biotech GmbH (Germany). Four first-generation libraries were built by PCR using trinucleotide oligonucleotides and KOD polymerase (Merck Millipore). For each library, 2 PCRs were required to cover the whole gene. For each PCR, 100 pmol primers and 100 ng DNA template were used in a 500 μl reactions. 25 cycles were performed, conditions according to KOD manual.

10 μg each PCR fragments were digested with 100 units BsaI (NEB) in 250 μl reaction, and incubated 1 h at 37° C. Approximately 5.5 pmol of each PCR fragment were ligated in 350 μl reaction with 1400 units T4 DNA ligase (NEB). A PCR was then performed to add the restriction sites required for cloning into the phagemid vector: 800 ng template DNA was amplified with both primers below, in 1 ml PCR reaction. 15 cycles were performed.

I. Library Construction

CH2 domain libraries were adapted by PCR to be subcloned into phagemid pIFF6 in frame with pIII. Briefly fragments for library #13, #15 and #16 and were digested with HF EcoRI/BamHI restriction enzymes (NEB), purified on Qiaquick columns (Qiagen) and ligated into the EcoRI/BamHI dephosphorylated phagemid O/N at 16° C. Ligations were phenol extracted, EtOH precipitated and transformed into TOP10F' electro-competent cells. Transformations were plated on 2×TY/Amp/2% glucose big square plates. Each library was ligated, transformed and plated separately and for each one was collected a number of clone equal or 10 fold superior to the theoretical diversity. Phage rescue was obtained infecting cells at O.D.$_{600}$0.5 with M13 K07 at a MOI of approximately 10. After o/n growth, cells were pelleted and phages in the supernatant purified through a CsCl gradient. After dialysis and titration, libraries were frozen in 10% DMSO and stored at −80° C. ready to use.

J. Libraries Selections Against EphA2

Selection against mEphA2 was carried out directly coating the recombinant protein (Fc chimera, R&D Systems) at 10 µg/well on Nunc Maxisorp ELISA plate. Libraries #13, #15 and #16 were pooled together and $10^{11}$ phages were pre-blocked in 5% milk/PBS1×/Tween 0.05% (MPBST) for 1 hr at RT, as well as the coated EphA2 protein. Then for the selection, phages were incubated for 1 hr at RT with the protein in MPBST; after extensive washings with PBST, the bound phages were eluted with Triethylamine (TEA) and used to infect 10 ml of a mid-log culture of TG1 cells. After 1 hr, a small aliquot was taken, diluted and plated out to titrate the number of selected clones. The remaining cells were centrifuged, resuspended into 1 ml of 2XTY and plated onto a 2×TYAG agar bioassay plate.

After o/n growth at 30° C., cells were harvest from the plate in 2XTY/16% glycerol and frozen at −80° C. For the next round of selection 50 ml of 2×TYAG were inoculated with 50 µl of selected clones, grown at 37° C. till OD$_{600}$=0.5 and superinfected with M13K07 at a MOI of 10.

After 1 hr of incubation at 37° C. the medium was changed, centrifuging the cells and resuspending them in 50 ml of 2×TYAK (ampicillin at 100 µg/ml and kanamycin at 25 µg/ml).

Amplified phages were recovered after o/n growth at 37° C. by centrifugation and 900 µl used for the next round of selection, following the procedure described above. During the screening either the phage pool from the different rounds of selection or the individual picked clones were tested in ΨElisa.

K. Affinity Maturation Libraries

The PCRs to amplify CH2 gene and introduce diversity in loop BC were performed as before. The clones selected from the phage selection, E10 and A9 were used as DNA template. The PCR fragments were digested and ligated together as before. The libraries were then digested with NotI, whereas the gene expressing repA was digested with Bsp120I. 5.5 pmol of library DNA and repA were ligated together in 350 µl reaction, with 1400 units ligase. A PCR was finally performed with a long primer adding the tac promoter upstream of the libraries (as described in Odegrip et al., 2004;): 1.8 µg of DNA was amplified in a lml PCR reaction, for 15 cycles. Correct library assembly was confirmed by sequencing.

L. ELISA Assays

Proteins were coated on Nunc maxisorp plates at the desired concentration in the range of 10 µg/ml in PBS1X, o/n at 4° C., then blocked with 3% Marvell/PBS for 1 hr, and incubated with pre-blocked phages in 3% MPBST for 1 hr at RT. After extensive washing with PBS/0.1% Tween, phage binding was detected by addition of α-M13-HRP mAb (Amersham) diluted 1:5000 in 3% MPBS incubated for an additional hour at RT. Development with TMB was followed by reading at OD450 nm.

When phages were tested for binding to cells, upon doxycycline induction EphA2 expressing HEK293 were fixed in 4% paraformaldehyde for 20', washed with PBS1X, blocked with 3% MPBS for 1 hr and incubated with phage supernatants for 2 hrs. Binding was revealed with αM13-HRP after 30' of development.

M. Localization Experiments Via Immunofluorescence Analysis

PC3 cells were seeded the day before at the density of 18.000 cells/well in 96 wells microtiter. The day after the plate were put at 4° C. for 10 minutes, then medium was removed and CH2s variants diluted in warm fresh media at 500 ng/well added. Binding was allowed at 4° C. for 30 min (T0). Then the internalization time course (at time 15 minutes, T15,T30,T60,T180) was started. At each time point media was removed, the cells were fixed with 2% PFA-PBS solution and incubate in the dark for 20 minutes at RT. After 5× washes in 1XPBS, cells were permeabilized with 3% BSA-PBS 0.1% Triton for 1 hr at RT.

The primary antibody was diluted in 3% BSA-PBS 0.1% Triton (αFlag 1:1000, αLAMP1 1:500) and incubated for 1 hr at RT. After 3 washings in PBS 0.1% Triton and a final wash in 1×PBS, the secondary αMouse-AF488 or the αRabbit-AF594 diluted 1:3000 in 3% BSA-PBS 0.1% Triton were added and incubated for 1 hr at RT. Washings were repeated as previously described. For the nuclear staining, cells were incubated with DAPI in 1×PBS 20 min in the dark.

Images were Acquired at INCELL.

N. Surface Plasmon Resonance Assay

All the SPR interaction analyses were performed by a Biacore 3000 instrument (GE Healthcare, Uppsala, Sweden). Human EphA 2 (hEphA2) (12 µg in 10 mM sodium acetate buffer pH 4.0) was immobilized on CM5 chip by amine coupling with a ligand density of 500 RU according to the manufacturer instructions. Briefly, the surface of sensor chip was activated for 7 min using a mixture of 0.1M NHS and 0.4M EDC, 1.2 µg/ml of hEphA2 in 10 mM sodium acetate (pH 4.0) was injected for 7 min at 10 µl/min, and residual activated groups on the surface were blocked by a 7-min injection of 1M ethanolamine (pH 8.5). The binding of CH2-chimeras to the immobilized ligand was evaluated by a multi cycle kinetic procedure in HBS-P running buffer (50 mM Hepes pH 7.4, 150 mM NaCl, 0.005% surfactant P-20) provided by the manufacturer. The analyte was injected over the ligand for 2.5 min at 40 µl/min until equilibrium and dissociation was monitored for 5 min. The sensor surface was regenerated with a pulse (30 sec) of 0.05M NaOH, 0.5M NaCl, 0.005% SDS, following by extensive washing (6 min, 40 µl/min). The collected data and the kinetic parameters were evaluated with BiaEvaluation software v 3.0. The experiments were repeated three times with similar results. All the reagents were purchased from GE Healthcare.

O. Phage Display

Phage selection was performed by coating the recombinant protein targets directly on the Nunc plates (cat#44-

2404). Briefly, 10 μg of mEphA2-Fc (R&D Systems, cat#639-A2) was coated in PBS1X O/N at 4° C. The day after, the well was washed with PBS1X to remove the excess of antigen and blocked for 1 hr at RT with Milk3% PBS1× (MPBS) to reduce non-specific phages binding to the plastic surface. In parallel, one aliquot of 1012 phages from the pool of libraries (the phage libraries #13, #15 and #16 were mixed respecting the different theoretical diversities) was blocked with 100 μl of MPBS for 1 hr at RT and then added to the wells. Phages were allowed to bind the antigens for 2 hrs at RT, then the solution was taken out, and washings steps with 1XPBS/0.05% Tween were performed.

The phases were eluted and bacteria were scraped from the bioassay plates into 10 ml 2XTYAG 50% Glycerol and used to rescue the phages for the next round of selection. 50 ml of 2XTYAG were inoculated with 50 μl of the scraping and grown at 37° C. up to OD600=0.5. Bacterial cells containing the phagemids were super-infected with the helper phage M13K07 to produce the selected phages. Cells were incubated with M13K07 30' at 37° C. in stationary, then 30' at 37° C. in gentle shaking, then cells were recovered by centrifugation to remove the supernatant, the medium was changed with 2XTY Amp 100 ug/ml Kan 25 ug/ml, and grown O/N at 25° C. at high shaking.

The day after, the supernatant, after centrifugation, was used for a new round of selection, following the procedure previously described. Starting from the second round, the so-called "input" at each selection round corresponds to the titer of phages amplified from the previous round that, in general, is around 1010-1011 phages/ml. After four consecutive rounds of selection, the reactivity of the pool of phages from each round was analyzed in phage-ELISA on mEphA2-Fc (1 μg/well).

P. CIS DNA Display

Selections were performed on mouse recombinant EphA2 (Fc chimera, R&D Systems), biotinylated using EZ-Link Sulfo-NHS-LC-Biotin (Pierce). Free biotin removed with Zeba Desalt Spin column (Pierce). Generally, in vitro transcription and translations (ITT) were carried out as previously described (Odegrip et al., 2004; Eldridge et al., 2009). 6 μg of DNA (3 $10^{12}$ molecules) were expressed in 200 μl ITT reaction. After expression, the samples were diluted 5-fold in selection buffer containing 2% bovine serum albumin (BSA), in phosphate-buffered saline (PBS). 83 nM biotinylated EphA2 was added to the blocked ITT reaction and incubated for 1 h at room temperature (RT) while mixing on a rotary mixer. 100 μl streptavidin coated magnetic beads (M280, Invitrogen) were then added for 15 min, to pull down the binders. The beads were then removed from the selection buffer and washed four times with 1 ml PBS-T (PBS, 0.1% Tween-20) and once with PBS (30 sec per wash). Bound DNA was eluted from the beads by incubation in 1× ThermoPol buffer (NEB), at 75° C. for 10 min. The eluted material was added to a recovery PCR reaction, thereby producing input DNA for the next round of selection.

For subsequent rounds of expression, the resulting DNA from the preceding round was added to a fresh ITT mixture and the selection process was repeated. The target concentration was decreased to 20 nM for the $2^{nd}$ round, 5 nM for the $3^{rd}$ round, 500 pM for the $4^{th}$ round and 50 pM for the $5^{th}$ round; washes were increased to 5 times 5 min for round 2 and 7 times 5 min for subsequent rounds.

The DNA outputs from rounds 3, 4 and 5 were cloned in pET33b and transformed in Shuffle cells (NEB) for cytoplasmic expression. After induction overnight at 20° C., the bacterial cells were lysed using BugBuster Master Mix (Merck Millipore), and the cytoplasmic fraction was diluted in blocking buffer (2% BSA in PBS).

Enzyme-linked immunosorbent assays (ELISAs) were then performed to screen for shCH2 that bound the target ligand. Maxisorp plates were coated with 500 ng per well of streptavidin in PBS overnight at 4° C. The plates where then coated with 50 ng per well of biotinylated EphA2 in PBS 30 min at room temperature. After blocking the plates with blocking buffer (2% BSA in PBS) for 1 h, the diluted lysate cells were added to the plates and incubated for 1 h at room temperature. CH2 domain binders were detected using horseradish peroxidase-conjugated anti-FLAG M2 antibody (Sigma) and TMB peroxidase substrate followed by detection and reading at 450 nm in an absorbance plate reader. A selection of positive clones that showed a high signal for EphA2, were sequenced by Sanger sequencing (Cogenics Ltd, UK) to obtain the shCH2 domain sequences.

Q. Protein Expression and Affinity Measurement

Affinity matured clones were expressed in Shuffle cells, and induced for 22 h at 20° C. with 0.5 mM IPTG. The cells were lysed with BugBuster Master Mix and the Abdurin domains were then purified on a HisTrap HP column using the ÄKTA Protein Purification Systems (GE Healthcare), followed by further purification through gel filtration Superdex 75 10/300 GL.

Real-time binding assays between the purified CH2 domains and human (R&D Systems) or mouse EphA2 were performed using biolayer interferometry with an Octet Red system (Fortebio, USA). The biotinylated EphA2 was immobilized on streptavidin biosensors at 15 μg/ml in Kinetics Buffer (ForteBio). Association curves were obtained by incubating target-coated biosensors with varying concentrations of the respective Abdurin domains (11-300 nM in Kinetics Buffer), and dissociations were detected by incubating in Kinetics Buffer. The data were fitted from steady state equilibrium data using Octet Data Analysis software.

R. Binding on Transfected Cells

CHOK1 cells were transfected with transfection-ready huEphA2 cDNA (Origene) according to manufacturer instruction. The CHO-EphA2 cells used in the binding assay were the progeny of a single cell clone, whose expression of EphA2 was verified by fluorescence-activated cell sorter (FACS) using a mouse anti-human EphA2 (R&D Systems). CH2 domains were incubated at different concentrations (1 nM to 7 μM) with CHO-EphA2 cells. Binding was then detected with mouse anti histidine tag/Fitc FITC antibody conjugate (AbD Serotec). Cells were washed and resuspended in FACS buffer (PBS, 1% BSA, 0.05% $NaN_3$) and 10,000 events were analyzed on the FACSJazz instrument (BD Biosciences).

S. Protein Chelation

MeCOSar, a metal ion chelator, was conjugated onto the B6 and B11 at a ratio of approximately 1:1. Stability of the conjugates was determined by HPLC at 2 weeks for aliquots stored at 2-8° C. The MeCOSar-modified CH2 domains, B6 and B11, and MeCOSar-mAb (control) conjugates were radiolabelled with $^{64}Cu$ prior to the animal imaging work. $^{64}Cu$ synthesis was performed. 500 μg of each MeCOSar-modified CH2 domains was incubated with 125 MBq at pH 7 and RT for 20 min and cleaned up (EDTA/DIMASAR) via spin columns (3K).

Analysis/Quality control was performed using thin layer chromatography (TLC) (silica gel 60, F254; Merck) and 10 mM EDTA, 0.1M PBS buffer as the mobile phase. Radiolabelled MeCOSar-modified CH2 domains were spotted at the origin, the strip was allowed to air-dry and was developed. The strip was cut into three pieces and the radioactivity in each section was counted using a gamma counter (Wizard single-detector gamma-counter, Perkin Elmer).

The MeCOSar-modified CH2 domains and MeCOSar-mAb conjugates were radiolabelled with Cobalt-57 and purified. Radio-HPLC was used to determine both conjugation and radiolabeling. Radiolabeling of the products was investigated for reproducibility and stability over 24 hrs, with quality control procedures as detailed previously.

The MeCOSar-modified CH2 domains and MeCOSar-mAb conjugates were then radiolabelled with $^{64}$Cu. $^{64}$Cu synthesis was performed. 500 µg of each MeCOSar-modified CH2 domains was incubated with 125 MBq at pH 7 and RT for 20 min and cleaned up (EDTA/DIMASAR) via spin columns (3K).

Analysis/Quality control was performed using thin layer chromatography (TLC) (silica gel 60, F254; Merck) and 10 mM EDTA, 0.1M PBS buffer as the mobile phase. Radiolabelled MeCOSar-modified CH2 domains were spotted at the origin, the strip was allowed to air-dry and was developed. The strip was cut into three pieces and the radioactivity in each section was counted using a gamma counter (Wizard single-detector gamma-counter, Perkin Elmer).

T. Animal Model

Twenty nude mice were inoculated with $2 \times 10^6$ human PC3 prostate cancer cells per animal in 100 µl PBS with 100 µl Matrigel. The inoculation resulted in palpable tumors in the majority of mice by day 4, and the tumors reached a volume of approximately 550 mm³ at Day 11. Tumors were very consistent between animals. There was no evidence of ulceration at the time of imaging, and the animals were bright and alert, in good condition apart from the tumors.

The study was performed over a number of weeks according to the following schedule:

TABLE 9

Radiolabelling and administration dates

| Administration date | Test Article | Test model |
|---|---|---|
| 20 May 2014 | $^{64}$Cu-MeCOSar-B6_CH2 | 1 × PC3 Mouse |
| 20 May 2014 | $^{64}$Cu-MeCOSar-B11_CH2 | 1 × PC3 Mouse |
| 3 Jun. 2014 | $^{64}$Cu-MeCOSar-B6_CH2 | 3 × PC3 Mice |
| 10 Jun. 2014 | $^{64}$Cu-MeCOSar-B6_CH2 | 3 × PC3 Mice |

A pilot imaging study was conducted with residual product from the radiolabeling confirmation step with mice that had been used to establish and confirm the suitability of the PC3 model. One mouse each was injected and imaged with 20 ug (~3.0 MBq) of B6 and B11. Although uptake was seen in the tumors at 48 hrs in the biodistribution data at sacrifice, no signal could be detected in the images. The dose was therefore increased for the full study, and PET scan time was extended.

Mice were anaesthetized in 2% isoflurane in a closed anesthetic induction chamber. The radiolabelled compounds the conjugated modified CH2 domains, B6 ($^{64}$Cu-MeCOSar-B6_CH2), and B12 ($^{64}$Cu-MeCOSar-B11_CH2) and the control $^{64}$Cu-MeCOSar-shWT_CH2 (total of ~100 µg of each CH2 modified domain -~15.0 MBq) were diluted with normal saline containing 0.9% sodium chloride and injected intravenously via tail vein.

U. PET/CT Imaging

The study was conducted using a Bioscan NanoPET-CT small animal imaging system. Post anesthetic, the mice were positioned on the scanner bed and PET scans were acquired using 30-45 minute static acquisitions. Micro-CT scans were subsequently acquired for anatomical co-registration which took approximately 20 minutes. PET scans were obtained at 4 hours, 24 hours and 48 hrs after injection of the radiotracer.

Four mice from each treatment group received intravenous $^{64}$Cu-MeCOSar-B6_CH2, $^{64}$Cu-MeCOSar-B11_CH2, $^{64}$Cu-MeCOSar-shWT_CH2, $^{64}$CuMeCOSar-shWTCH2 or $^{64}$CuMeCOSar-IgG. After the last scan (48 h time point), animals were perfused, several organs including tumor and muscle were removed and the level of radioactivity measured by a gamma-counter. Radioactivity concentrations in the PET images were recalculated to provide data of Standardized Uptake Value (SUV) by dividing the radioactivity concentration (Bq/ml) by the injected radioactivity (Bq) per body weight (g).

The invention claimed is:

1. A modified isolated immunoglobulin CH2 domain that specifically binds to an
extracellular region of an EphA2 receptor,
wherein the amino acid sequence of the modified immunoglobulin CH2 domain comprises at least one amino acid substitution or deletion in comparison to a wild type immunoglobulin CH2 domain amino acid sequence, wherein the wild type immunoglobulin CH2 domain amino acid sequence comprises a human wild type immunoglobulin CH2 domain amino acid sequence of SEQ ID NO: 1or a macaque wild type immunoglobulin CH2 domain amino acid sequence of SEQ ID NO: 2,
wherein the modified isolated immunoglobulin CH2 domain comprises: a framework 1 region, a framework 2 region, a framework 3 region, a framework 4 region, a loop 1 amino acid sequence located between the framework 1 region and the framework 2 region, a loop 2 amino acid sequence located between the framework 2 region and the framework 3 region, and a loop 3 amino acid sequence located between the framework 3 region and the framework 4 region,
wherein the at least one amino acid substitution comprises amino acid substitutions in the loop 2 amino acid sequence, wherein the loop 2 amino acid sequence comprising the at least one amino acid substitutions comprises an amino acid sequence selected from the group consisting of SEQ ID NOs: 22-28, and wherein the modified isolated immunoglobulin CH2 domain has a substitution at position 1 of the framework 3 region.

2. The modified isolated immunoglobulin CH2 domain of claim 1, wherein the wild type immunoglobulin CH2 domain amino acid sequence comprises SEQ ID NO: 1.

3. The modified isolated immunoglobulin CH2 domain of claim 1, wherein the wild type immunoglobulin CH2 domain amino acid sequence comprises SEQ ID NO: 2.

4. The modified isolated immunoglobulin CH2 domain of claim 1, further comprising at least one amino acid substitution in the loop 1 amino acid sequence.

5. The modified isolated immunoglobulin CH2 domain of claim 4, wherein the at least one amino acid substitution in the loop 1 amino acid sequence comprises an amino acid substitution at positions 2-7 of the human wild type loop 1 amino acid sequence of SEQ ID NO: 3 or the macaque wild type loop 1 amino acid sequence of SEQ ID NO: 6.

6. The modified isolated immunoglobulin CH2 domain of claim 1, wherein the loop 1 amino acid sequence is selected from the group consisting of SEQ ID NOS: 14-15, 17-21, SEQ ID NOS: 85-86 and 94-99 and wherein the loop 2 amino acid sequence is selected from the group consisting of SEQ ID NOS: 22-23; or wherein the loop 1 amino acid sequence comprises SEQ ID NO: 3 substituted at positions 2-7 with the amino acid sequence of SEQ ID NO: 53 and wherein the loop 2 amino acid sequence is selected from the group consisting of SEQ ID NOS: 22-23.

7. The modified isolated immunoglobulin CH2 domain of claim 1, wherein the framework 3 region is SEQ ID NO: 12 or SEQ ID NO: 101.

8. The modified isolated immunoglobulin CH2 domain of claim 1, wherein the modified isolated immunoglobulin CH2 domain is selected from the group consisting of SEQ ID NOS: 29-32, 34-38 and SEQ ID NOS: 87-88 or wherein the modified isolated immunoglobulin CH2 domain comprises SEQ ID NO: 3 substituted at positions 2-7 with the amino acid sequence of SEQ ID NO: 53.

9. The modified isolated immunoglobulin CH2 domain of claim 1, wherein the modified isolated immunoglobulin CH2 domain binds FcRn.

10. The modified isolated immunoglobulin CH2 domain of claim 1, wherein the modified isolated immunoglobulin CH2 domain is a deimmunized CH2 domain.

11. The modified isolated immunoglobulin CH2 domain of claim 10, wherein the deimmunized CH2 domain is a modified macaque IgG immunoglobulin CH2 domain.

12. The modified isolated immunoglobulin CH2 domain of claim 1, wherein the modified isolated immunoglobulin CH2 domain further comprises at least one amino acid addition or substitution located at the N-terminus, C-terminus or both termini.

13. The modified isolated immunoglobulin CH2 domain of claim 12, wherein the modified isolated immunoglobulin CH2 domain is selected from the group consisting of SEQ ID NOS: 89-93.

14. The modified isolated immunoglobulin CH2 domain of claim 1, wherein the modified isolated immunoglobulin CH2 domain further comprises a first amino acid substitution and a second amino acid substitution, wherein the first amino acid substitution and the second amino acid substitution are cysteine residues, and wherein the cysteine residues form a disulfide bond.

15. The modified isolated immunoglobulin CH2 domain of claim 14,
wherein the first amino acid substitution is at position 12 and the second amino acid substitution is at position 104 or
wherein the first amino acid substitution is at position 10 and the second amino acid substitution is at position 102 of the human wild type immunoglobulin CH2 domain of SEQ ID NO: 1 or of the macaque wild type immunoglobulin CH2 domain of SEQ ID NO: 2.

16. The modified isolated immunoglobulin CH2 domain of claim 1, wherein the modified isolated immunoglobulin CH2 domain further comprises an N-terminal deletion of 6 amino acids.

17. The modified isolated immunoglobulin CH2 domain of claim 1, wherein the modified isolated immunoglobulin CH2 domain further comprises an N-terminal deletion of 1-7 amino acids.

18. The modified isolated immunoglobulin CH2 domain of claim 1, wherein the modified isolated immunoglobulin CH2 domain further comprises a 1-4 amino acid C-terminal deletion.

19. The modified isolated immunoglobulin CH2 domain of claim 9, wherein the FcRn is a human FcRn.

20. The modified isolated immunoglobulin CH2 domain of claim 1, wherein the modified isolated immunoglobulin CH2 domain is detectably labeled with a radioisotope, a fluorescent compound, a chemiluminescent compound, an enzyme, an imaging agent or a metal ion.

21. An immunoconjugate comprising a modified isolated immunoglobulin CH2 domain that specifically binds to an EphA2 receptor according to claim 1 and a toxin or a small molecule,
wherein the modified isolated immunoglobulin CH2 domain is fused to the toxin or wherein the modified isolated immunoglobulin CH2 domain is joined to the small molecule.

22. The immunoconjugate of claim 21, wherein the toxin is a fungal ribonuclease.

23. The immunoconjugate of claim 22, wherein the fungal ribonuclease is α-sarcin or a deimmunized α-sarcin.

24. The modified isolated immunoglobulin CH2 domain or immunoconjugate of claim 1, wherein the EphA2 receptor is a human EphA2 receptor.

25. The modified isolated immunoglobulin CH2 domain or immunoconjugate of claim 1, wherein the EphA2 receptor is a mouse EphA2 receptor.

26. A pharmaceutical composition comprising:
the modified isolated immunoglobulin CH2 domain or the immunoconjugate of claim 1, and
a pharmaceutical carrier.

27. The immunoconjugate of claim 21, wherein the small molecule is a compound selected from the group consisting of auristatins, maytansinoids and pyrrolobenzodiazepines.

* * * * *

SEQUENCE LISTING

```
<160> NUMBER OF SEQ ID NOS: 101

<210> SEQ ID NO 1
<211> LENGTH: 110
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 2
<211> LENGTH: 110
<212> TYPE: PRT
<213> ORGANISM: Macaca sp.

<400> SEQUENCE: 2

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Asp Val Lys Phe Asn Trp Tyr
             35                  40                  45

Val Asn Gly Ala Glu Val His His Ala Gln Thr Lys Pro Arg Glu Thr
         50                  55                  60

Gln Tyr Asn Ser Thr Tyr Arg Val Val Ser Val Leu Thr Val Thr His
 65                  70                  75                  80

Gln Asp Trp Leu Asn Gly Lys Glu Tyr Thr Cys Lys Val Ser Asn Lys
                 85                  90                  95

Ala Leu Pro Ala Pro Ile Gln Lys Thr Ile Ser Lys Asp Lys
            100                 105                 110

<210> SEQ ID NO 3
<211> LENGTH: 10
<212> TYPE: PRT
<213> ORGANISM: Homo sapiens

<400> SEQUENCE: 3

Asp Val Ser His Glu Asp Pro Glu Val Lys
  1               5                  10

<210> SEQ ID NO 4
<211> LENGTH: 6
<212> TYPE: PRT
<213> ORGANISM: Homo sapiens

<400> SEQUENCE: 4

Glu Glu Gln Tyr Asn Ser
  1               5

<210> SEQ ID NO 5
<211> LENGTH: 9
<212> TYPE: PRT
<213> ORGANISM: Homo sapiens

<400> SEQUENCE: 5

Ser Asn Lys Ala Leu Pro Ala Pro Ile
  1               5

<210> SEQ ID NO 6
<211> LENGTH: 10
<212> TYPE: PRT
<213> ORGANISM: Macaca sp.

<400> SEQUENCE: 6
```

```
Asp Val Ser Gln Glu Asp Pro Asp Val Lys
1               5                  10

<210> SEQ ID NO 7
<211> LENGTH: 6
<212> TYPE: PRT
<213> ORGANISM: Macaca sp.

<400> SEQUENCE: 7

Glu Thr Gln Tyr Asn Ser
1               5

<210> SEQ ID NO 8
<211> LENGTH: 9
<212> TYPE: PRT
<213> ORGANISM: Macaca sp.

<400> SEQUENCE: 8

Ser Asn Lys Ala Leu Pro Ala Pro Ile
1               5

<210> SEQ ID NO 9
<211> LENGTH: 28
<212> TYPE: PRT
<213> ORGANISM: Homo sapiens

<400> SEQUENCE: 9

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val
            20                  25

<210> SEQ ID NO 10
<211> LENGTH: 18
<212> TYPE: PRT
<213> ORGANISM: Homo sapiens

<400> SEQUENCE: 10

Phe Asn Trp Tyr Val Asp Gly Ala Glu Val His His Ala Gln Thr Lys
1               5                   10                  15

Pro Arg

<210> SEQ ID NO 11
<211> LENGTH: 25
<212> TYPE: PRT
<213> ORGANISM: Homo sapiens

<400> SEQUENCE: 11

Thr Tyr Arg Val Val Ser Val Leu Thr Val Leu His Gln Asp Trp Leu
1               5                   10                  15

Asn Gly Lys Glu Tyr Lys Cys Lys Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Tyr Arg Val Val Ser Val Leu Thr Val Leu His Gln Asp Trp Leu
1               5                   10                  15
```

Asn Gly Lys Glu Tyr Lys Cys Lys Val
            20                  25

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Lys Thr Ile Ser Lys Ala Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Tyr Glu Ala Ala Ala Leu Glu Val Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Pro His Leu Gly Val Asp Glu Val Lys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Pro Tyr Leu His Asp Glu Val Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Tyr Arg Ala Asp Tyr Leu Glu Val Lys
1               5                   10

<210> SEQ ID NO 18
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 18

Asp Tyr Asp Leu Pro Arg Ser Glu Val Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Tyr Asp Gln Arg Arg Leu Glu Val Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Tyr Glu Leu Gln Arg Leu Glu Val Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Arg Glu Pro Tyr Leu Glu Val Lys
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Tyr Asp Pro Leu Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Val Asp Pro Leu Gly
1               5
```

```
<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Tyr Ala Leu Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Tyr Tyr Ala Leu Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Tyr Tyr Ala Leu Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Arg Tyr Val Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Leu Asp Pro Leu Tyr
1               5

<210> SEQ ID NO 29
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 29

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 30
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Ala Glu Val
        35                  40                  45

His His Ala Gln Thr Lys Pro Arg Arg Val Asp Pro Leu Gly Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 31
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Glu Ala
            20                  25                  30

Ala Ala Leu Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly

```
                65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 32
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Pro Ser Val Phe Leu Phe Pro Pro Lys Pro Lys Asp Thr Leu Met
1               5                   10                  15

Ile Ser Arg Thr Pro Glu Val Thr Cys Val Val Asp Pro His Leu
            20                  25                  30

Gly Val Asp Glu Val Lys Phe Asn Trp Tyr Val Asp Gly Ala Glu Val
            35                  40                  45

His His Ala Gln Thr Lys Pro Arg Gln Tyr Asp Pro Leu Tyr Gly Tyr
        50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 33
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Pro Ser Val Phe Leu Phe Pro Pro Lys Pro Lys Asp Thr Leu Met
1               5                   10                  15

Ile Ser Arg Thr Pro Glu Val Thr Cys Val Val Asp Pro Tyr Leu
            20                  25                  30

His Asp Glu Val Lys Phe Asn Trp Tyr Val Asp Gly Ala Glu Val His
            35                  40                  45

His Ala Gln Thr Lys Pro Arg Gln Tyr Asp Pro Leu Tyr Gly Tyr Arg
        50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys
            100

<210> SEQ ID NO 34
<211> LENGTH: 104
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 34

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Arg Ala
            20                  25                  30

Asp Tyr Leu Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 35
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Asp Leu
            20                  25                  30

Pro Arg Ser Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 36
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Asp Gln
            20                  25                  30

Arg Arg Leu Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 37
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Glu Leu
            20                  25                  30

Gln Arg Leu Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 38
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Arg Glu
            20                  25                  30

Pro Tyr Leu Glu Val Lys Phe Asn Trp Tyr Val Asp Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys
            100

<210> SEQ ID NO 39
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 39

Xaa Xaa Asp Pro Leu Xaa Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 40

Xaa Tyr Tyr Ala Leu Gly Gly
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 41

Tyr Xaa Ala Xaa Xaa Leu
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 42

Pro Xaa Leu Xaa Xaa Asp
1               5
```

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Val Asp Pro Leu Gly Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Tyr Asp Pro Leu Tyr Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Leu Asp Pro Leu Tyr Gly
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Tyr Ala Leu Gly Gly
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Tyr Tyr Ala Leu Gly Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 48

Ala Tyr Tyr Ala Leu Gly Gly
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Arg Tyr Val Ser Tyr Val
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Glu Ala Ala Ala Leu
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Arg Ala Asp Tyr Leu
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro His Leu Gly Val Asp
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Tyr Leu His Asp Asp
1               5

<210> SEQ ID NO 54
<211> LENGTH: 28
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 54

Gly Pro Asp Val Phe Leu Phe Pro Pro Lys Pro Lys Asp Thr Leu Met
1               5                   10                  15

Ile Ser Arg Thr Pro Glu Val Thr Cys Val Val Val
            20                  25

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Asn Lys Ala Leu Pro Ala Pro Glu
1               5

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Pro Ser Val Phe Cys Phe Pro Pro Lys Pro Lys Asp Thr Leu Met
1               5                   10                  15

Ile Ser Arg Thr Pro Glu Val Thr Cys Val Val Val
            20                  25

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Cys Thr Ile Ser Lys Ala Lys
1               5

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Pro Ser Cys Phe Leu Phe Pro Pro Lys Pro Lys Asp Thr Leu Met
1               5                   10                  15

Ile Ser Arg Thr Pro Glu Val Thr Cys Val Val Val
            20                  25

<210> SEQ ID NO 59
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 59

Ser Asn Lys Ala Leu Pro Ala Pro Cys
1               5

<210> SEQ ID NO 60
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Ser Cys Asp Lys Thr His Thr Ala Pro Glu Lys Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val
            35                  40

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Lys Thr Ile Ser Lys Ala Cys
1               5

<210> SEQ ID NO 62
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Lys or Ala

<400> SEQUENCE: 62

Ala Val Thr Trp Thr Cys Leu Asn Asp Xaa Lys Asn Pro Lys Thr Asn
1               5                   10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
            35                  40                  45

Pro His Trp Phe Thr Asn Gly Tyr Asp Gly Asp Gly Lys Leu Pro Lys
        50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110
```

```
Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Gln Gly Glu
        130                 135                 140

Leu Lys Leu Cys Ser His
145                 150

<210> SEQ ID NO 63
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Arg, Lys or Ala

<400> SEQUENCE: 63

Ala Val Thr Trp Thr Cys Leu Asn Asp Gln Lys Asn Pro Lys Thr Xaa
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Gln Gly Glu
        130                 135                 140

Leu Lys Leu Cys Ser His
145                 150

<210> SEQ ID NO 64
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Lys or Arg

<400> SEQUENCE: 64

Ala Val Thr Trp Thr Cys Leu Asn Asp Gln Lys Asn Pro Lys Thr Asn
1               5                   10                  15

Lys Xaa Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45
```

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Gln Gly Glu
    130                 135                 140

Leu Lys Leu Cys Ser His
145                 150

<210> SEQ ID NO 65
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Asp or Glu

<400> SEQUENCE: 65

Ala Val Thr Trp Thr Cys Leu Asn Asp Gln Lys Asn Pro Lys Thr Asn
 1               5                  10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
                35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Xaa Glu Asn Gln Gly Glu
    130                 135                 140

Leu Lys Leu Cys Ser His
145                 150

<210> SEQ ID NO 66
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Val Thr Trp Thr Cys Leu Asn Asp Gln Lys Asn Pro Lys Thr Asn
 1               5                  10                  15

```
Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Asp Asn Gln Gly Glu
    130                 135                 140

Leu Lys Leu Cys Ser His
145                 150

<210> SEQ ID NO 67
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (142)..(142)
<223> OTHER INFORMATION: Asn, Thr or Glu

<400> SEQUENCE: 67

Ala Val Thr Trp Thr Cys Leu Asn Asp Gln Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Glu Asn Xaa Gly Glu
    130                 135                 140

Leu Lys Leu Cys Ser His
145                 150

<210> SEQ ID NO 68
<211> LENGTH: 150
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Asp or Glu

<400> SEQUENCE: 68

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Xaa Glu Asn Gln Gly Glu
    130                 135                 140

Leu Lys Leu Cys Ser His
145                 150

<210> SEQ ID NO 69
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Asp or Glu

<400> SEQUENCE: 69

Ala Val Thr Trp Thr Cys Leu Asn Asp Gln Lys Asn Pro Lys Thr Arg
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Xaa Glu Asn Gln Gly Glu

```
      130                 135                 140

Leu Lys Leu Cys Ser His
145                 150

<210> SEQ ID NO 70
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Lys or Arg
<220> FEATURE:
<221> NAME/KEY: MOD_RES
<222> LOCATION: (139)..(139)
<223> OTHER INFORMATION: Asp or Glu

<400> SEQUENCE: 70

Ala Val Thr Trp Thr Cys Leu Asn Asp Gln Lys Asn Pro Lys Thr Asn
1               5                   10                  15

Lys Xaa Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
            35                  40                  45

Pro His Trp Phe Thr Asn Gly Tyr Asp Gly Asp Gly Lys Leu Pro Lys
        50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Xaa Glu Asn Gln Gly Glu
        130                 135                 140

Leu Lys Leu Cys Ser His
145                 150

<210> SEQ ID NO 71
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
            35                  40                  45

Pro His Trp Phe Thr Asn Gly Tyr Asp Gly Asp Gly Lys Leu Pro Lys
        50                  55                  60

Gly Arg Thr Pro Ile Lys Phe Gly Lys Ser Asp Cys Asp Arg Pro Pro
65                  70                  75                  80
```

```
Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Glu Asn Thr Gly Glu
    130                 135                 140

Leu Lys Leu Cys Ser His
145                 150

<210> SEQ ID NO 72
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Asp Glu Asn Thr Gly Glu
    130                 135                 140

Leu Lys Leu Cys Ser His
145                 150

<210> SEQ ID NO 73
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60
```

```
Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Glu Glu Asn Thr Gly Glu
        130                 135                 140

Leu Lys Leu Cys Ser His
145                 150

<210> SEQ ID NO 74
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ala Val Thr Trp Thr Cys Leu Asn Asp Gln Lys Asn Pro Lys Thr Arg
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Asp Glu Asn Thr Gly Glu
        130                 135                 140

Leu Lys Leu Cys Ser His
145                 150

<210> SEQ ID NO 75
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ala Val Thr Trp Thr Cys Leu Asn Asp Gln Lys Asn Pro Lys Thr Arg
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45
```

```
Pro His Trp Phe Thr Asn Gly Tyr Asp Gly Asp Gly Lys Leu Pro Lys
        50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Glu Glu Asn Thr Gly Glu
        130                 135                 140

Leu Lys Leu Cys Ser His
145                 150

<210> SEQ ID NO 76
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Val Thr Trp Thr Cys Leu Asn Thr Gln Lys Asn Pro Lys Thr Asn
 1               5                  10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
            35                  40                  45

Pro His Trp Phe Thr Asn Gly Tyr Asp Gly Asp Gly Lys Leu Pro Lys
        50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Thr Gly Glu
        130                 135                 140

Leu Lys Leu Cys Ser His
145                 150

<210> SEQ ID NO 77
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ala Val Thr Trp Thr Cys Leu Asn Asp Ala Lys Asn Pro Lys Thr Asn
 1               5                  10                  15

Lys Tyr Glu Thr Lys Arg Leu Leu Tyr Asn Gln Asn Lys Ala Glu Ser
                20                  25                  30
```

```
Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Thr Gly Glu
        130                 135                 140

Leu Lys Leu Cys Ser His
145                 150

<210> SEQ ID NO 78
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Val Thr Trp Thr Cys Leu Asn Asp Gln Lys Asn Ile Lys Thr Asn
1               5                   10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Thr Gly Glu
        130                 135                 140

Leu Lys Leu Cys Ser His
145                 150

<210> SEQ ID NO 79
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ala Val Thr Trp Thr Cys Leu Asn Asp Gln Lys Asn Pro Lys Gly Asn
1               5                   10                  15
```

-continued

```
Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Glu Asn Thr Gly Glu
    130                 135                 140

Leu Lys Leu Cys Ser His
145                 150

<210> SEQ ID NO 80
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ala Val Thr Trp Thr Cys Leu Asn Asp Gln Lys Asn Pro Lys Thr Asn
1               5                   10                  15

Lys Lys Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Glu Asn Thr Gly Glu
    130                 135                 140

Leu Lys Leu Cys Ser His
145                 150

<210> SEQ ID NO 81
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81
```

Ala Val Thr Trp Thr Cys Leu Asn Asp Gln Lys Asn Pro Lys Thr Ala
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Thr Gly Glu
    130                 135                 140

Leu Lys Leu Cys Ser His
145                 150

<210> SEQ ID NO 82
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Val Thr Trp Thr Cys Leu Asn Asp Gln Lys Asn Pro Lys Thr Asn
1               5                   10                  15

Lys Arg Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Thr Gly Glu
    130                 135                 140

Leu Lys Leu Cys Ser His
145                 150

<210> SEQ ID NO 83
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Ala Val Thr Trp Thr Cys Leu Asn Asp Gln Lys Asn Pro Lys Gly Asn
1               5                   10                  15
Lys Tyr Glu Thr Lys Arg Leu Leu Tyr Asn Gln Asn Lys Ala Glu Ser
            20                  25                  30
Asn Ser His His Ala Pro Leu Ser Asp Gly Lys Thr Gly Ser Ser Tyr
        35                  40                  45
Pro His Trp Phe Thr Asn Gly Tyr Asp Gly Asp Gly Lys Leu Pro Lys
    50                  55                  60
Gly Arg Thr Pro Ile Lys Phe Gly Lys Ser Asp Cys Asp Arg Pro Pro
65                  70                  75                  80
Lys His Ser Lys Asp Gly Asn Gly Lys Thr Asp His Tyr Leu Leu Glu
                85                  90                  95
Phe Pro Thr Phe Pro Asp Gly His Asp Tyr Lys Phe Asp Ser Lys Lys
            100                 105                 110
Pro Lys Glu Asn Pro Gly Pro Ala Arg Val Ile Tyr Thr Tyr Pro Asn
        115                 120                 125
Lys Val Phe Cys Gly Ile Ile Ala His Thr Lys Glu Asn Gly Gly Glu
    130                 135                 140
Leu Lys Leu Cys Ser His
145                 150
```

<210> SEQ ID NO 84
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Ala Val Thr Trp Thr Cys Leu Asn Asp Gln Lys Asn Pro Lys Gly Asn
1               5                   10                  15
Lys Tyr Glu Thr Lys Arg Leu Leu Tyr Asn Gln Asn Lys Ala Glu Ser
            20                  25                  30
Asn Ser His His Ala Pro Leu Ser Asp Gly Lys Thr Gly Ser Ser Tyr
        35                  40                  45
Pro His Trp Phe Thr Asn Gly Tyr Asp Gly Asp Gly Lys Leu Pro Lys
    50                  55                  60
Gly Arg Thr Pro Ile Lys Phe Gly Lys Ser Asp Cys Asp Arg Pro Pro
65                  70                  75                  80
Lys His Ser Lys Asp Gly Asn Gly Lys Thr Asp His Tyr Leu Leu Glu
                85                  90                  95
Phe Pro Thr Phe Pro Asp Gly His Asp Tyr Lys Phe Asp Ser Lys Lys
            100                 105                 110
Pro Lys Glu Asn Pro Gly Pro Ala Arg Val Ile Tyr Thr Tyr Pro Asn
        115                 120                 125
Lys Val Phe Cys Gly Ile Ile Ala His Thr Lys Asp Asn Gln Gly Glu
    130                 135                 140
Leu Lys Leu Cys Ser His
145                 150
```

<210> SEQ ID NO 85
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 85

Asp Tyr Arg Ala Asp Tyr Leu Asp Val Lys
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Pro His Leu Gly Val Asp Asp Lys
1               5

<210> SEQ ID NO 87
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Arg Ala
                20                  25                  30

Asp Tyr Leu Asp Val Lys Phe Asn Trp Tyr Val Asn Gly Ala Glu Val
            35                  40                  45

His His Ala Gln Thr Lys Pro Arg Gln Tyr Asp Pro Leu Tyr Gly Tyr
        50                  55                  60

Arg Val Val Ser Val Leu Thr Val Thr His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Gln Lys Thr Ile Ser Lys Asp Lys
            100

<210> SEQ ID NO 88
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Pro His Leu
                20                  25                  30

Gly Val Asp Asp Val Lys Phe Asn Trp Tyr Val Asn Gly Ala Glu Val
            35                  40                  45

His His Ala Gln Thr Lys Pro Arg Gln Tyr Asp Pro Leu Tyr Gly Tyr
        50                  55                  60
```

```
Arg Val Val Ser Val Leu Thr Val Thr His Gln Asp Trp Leu Asn Gly
 65                  70                  75                  80

Lys Glu Tyr Thr Cys Lys Val Ser Asn Lys Ala Leu Pro Ala Pro Ile
                 85                  90                  95

Gln Lys Thr Ile Ser Lys Asp Lys
            100
```

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Gly Ser Cys Asp Lys Thr His Thr Ala Pro Glu Lys Lys Gly Gly Pro
 1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Asp Tyr Arg Ala Asp Tyr
         35                  40                  45

Leu Asp Val Lys Phe Asn Trp Tyr Val Asn Gly Ala Glu Val His His
 50                  55                  60

Ala Gln Thr Lys Pro Arg Gln Tyr Asp Pro Leu Tyr Gly Tyr Arg Val
 65                  70                  75                  80

Val Ser Val Leu Thr Val Thr His Gln Asp Trp Leu Asn Gly Lys Glu
                 85                  90                  95

Tyr Thr Cys Lys Val Ser Asn Lys Ala Leu Pro Ala Pro Ile Gln Lys
             100                 105                 110

Thr Ile Ser Lys Asp Cys
            115
```

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Gly Ser Cys Asp Lys Thr His Thr Ala Pro Glu Lys Lys Gly Gly Pro
 1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Asp Tyr Arg Ala Asp Tyr
         35                  40                  45

Leu Asp Val Lys Phe Asn Trp Tyr Val Asn Gly Ala Glu Val His His
 50                  55                  60

Ala Gln Thr Lys Pro Arg Gln Tyr Asp Pro Leu Tyr Gly Tyr Arg Val
 65                  70                  75                  80

Val Ser Val Leu Thr Val Thr His Gln Asp Trp Leu Asn Gly Lys Glu
                 85                  90                  95

Tyr Thr Cys Lys Val Ser Asn Lys Ala Leu Pro Ala Pro Ile Gln Lys
             100                 105                 110

Thr Ile Ser Lys Asp Lys
            115
```

```
<210> SEQ ID NO 91
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Tyr Arg Ala
            20                  25                  30

Asp Tyr Leu Asp Val Lys Phe Asn Trp Tyr Val Asn Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Thr His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Gln Lys Thr Ile Ser Lys Asp Cys
            100

<210> SEQ ID NO 92
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Pro His Leu
            20                  25                  30

Gly Val Asp Asp Val Lys Phe Asn Trp Tyr Val Asn Gly Ala Glu Val
        35                  40                  45

His His Ala Gln Thr Lys Pro Arg Gln Tyr Asp Pro Leu Tyr Gly Tyr
    50                  55                  60

Arg Val Val Ser Val Leu Thr Val Thr His Gln Asp Trp Leu Asn Gly
65                  70                  75                  80

Lys Glu Tyr Thr Cys Lys Val Ser Asn Lys Ala Leu Pro Ala Pro Ile
                85                  90                  95

Gln Lys Thr Ile Ser Lys Asp Cys
            100

<210> SEQ ID NO 93
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
```

```
                    20                  25                  30

Glu Asp Pro Asp Val Lys Phe Asn Trp Tyr Val Asn Gly Ala Glu Val
                35                  40                  45

His His Ala Gln Thr Lys Pro Arg Glu Thr Gln Tyr Asn Ser Thr Tyr
 50                  55                  60

Arg Val Val Ser Val Leu Thr Val Thr His Gln Asp Trp Leu Asn Gly
 65                  70                  75                  80

Lys Glu Tyr Thr Cys Lys Val Ser Asn Lys Ala Leu Pro Ala Pro Ile
                    85                  90                  95

Gln Lys Thr Ile Ser Lys Asp Cys
                100

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Tyr Glu Ala Ala Leu Asp Val Lys
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Pro Tyr Leu His Asp Asp Val Lys
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Tyr Asp Leu Pro Arg Ser Asp Val Lys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Tyr Asp Gln Arg Arg Leu Asp Val Lys
1               5                   10

<210> SEQ ID NO 98
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 98

Asp Tyr Glu Leu Gln Arg Leu Asp Val Lys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Tyr Arg Glu Pro Tyr Leu Asp Val Lys
1               5                   10

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Tyr Arg Val Val Ser Val Leu Thr Val Thr His Gln Asp Trp Leu
1               5                   10                  15

Asn Gly Lys Glu Tyr Thr Cys Lys Val
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Tyr Arg Val Val Ser Val Leu Thr Val Thr His Gln Asp Trp Leu
1               5                   10                  15

Asn Gly Lys Glu Tyr Thr Cys Lys Val
            20                  25
```